United States Patent [19]
Baker et al.

[11] Patent Number: 5,567,726
[45] Date of Patent: Oct. 22, 1996

[54] IMIDAZOLE, TRIAZOLE AND TETRAZOLE DERIVATIVES

[75] Inventors: Raymond Baker, Much Hadham; Jose L. Castro Pineiro; Alexander R. Guiblin, both of Harlow; Austin J. Reeve, Great Dunmow; Francine Sternfeld, London; Victor G. Matassa, Furneux Pelham; Leslie J. Street, Harlow, all of United Kingdom

[73] Assignee: Merck, Sharp & Dohme Ltd., Hoddesdon, England

[21] Appl. No.: 374,582

[22] PCT Filed: Jul. 15, 1993

[86] PCT No.: PCT/GB93/01495

§ 371 Date: Jan. 24, 1995

§ 102(e) Date: Jan. 24, 1995

[87] PCT Pub. No.: WO94/02477

PCT Pub. Date: Feb. 3, 1994

[30] Foreign Application Priority Data

Jul. 24, 1992 [GB]  United Kingdom ............... 9215721
Dec. 8, 1992 [GB]  United Kingdom ............... 9225657

[51] Int. Cl.$^6$ ..................... A61K 31/415; C07D 403/04
[52] U.S. Cl. ..................... 514/383; 548/266.4; 548/466; 548/468
[58] Field of Search ............... 548/266.4, 466, 548/468; 514/383

[56] References Cited

U.S. PATENT DOCUMENTS 5,451,588  9/1995  Baker et al. ..................... 514/323

FOREIGN PATENT DOCUMENTS

0313397A1  4/1989  European Pat. Off.
0497512A3  8/1992  European Pat. Off.
WO91/18897  12/1991  WIPO.

*Primary Examiner*—Jacqueline Haley
*Attorney, Agent, or Firm*—Robert J. North; Melvin Winokur

[57] ABSTRACT

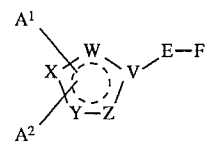 (I)

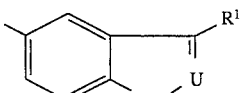

(a)

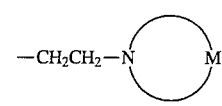

(i)

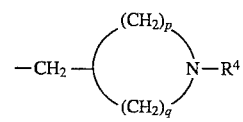

(ii)

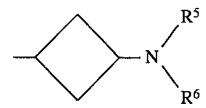

(iii)

Imidazole, triazole and tetrazole derivatives of formula (I) are selective agonists of 5-HT$_1$-like receptors and are therefore useful in the treatment of clinical conditions, in particular migraine and associated disorders, for which a selective agonist of these receptors is indicated, wherein the broken circle represents two non-adjacent double bonds in any position in the five-membered ring; two, three or four of V, W, X, Y and Z represent nitrogen and the remainder represent carbon provided that, when two of V, W, X, Y and Z represent nitrogen and the remainder represent carbon, then the said nitrogen atoms are in non-adjacent positions within the five-membered ring; E represents a bond or a straight or branched alkylene chain containing from 1 to 4 carbon atoms; F represents a group of formula (a); U represents nitrogen or C—R$^2$; B represents oxygen, sulphur or N—R$^3$; R$^1$ represents a group of formula (i), (ii) or (iii).

9 Claims, No Drawings

IMIDAZOLE, TRIAZOLE AND TETRAZOLE DERIVATIVES

This application is a 371 of PCT/GB93/01495 filed 15 Jul. 1993, now WO 94/02477 published 3 Feb. 1994.

The present invention relates to a class of substituted imidazole, triazole and tetrazole derivatives which act on 5-hydroxytryptamine (5-HT) receptors, being selective agonists of so-called "5-$HT_1$-like" receptors. They are therefore useful in the treatment of clinical conditions for which a selective agonist of these receptors is indicated.

5-$HT_1$-like receptor agonists which exhibit selective vasoconstrictor activity have recently been described as being of use in the treatment of migraine (see, for example, A. Doenicke et al., *The. Lancet,* 1988, Vol. 1, 1309–11). The compounds of the present invention, being selective 5-$HT_1$-like receptor agonists, are accordingly of particular use in the treatment of migraine and associated conditions, e.g. cluster headache, chronic paroxysmal hemicrania, headache associated with vascular disorders, tension headache and paediatric migraine.

EP-A-0313397 and WO-A-91/18897 describe separate classes of tryptamine derivatives substituted by various five-membered heteroaliphatic rings, which are stated to be specific to a particular type of "5-$HT_1$-like" receptor and thus to be effective therapeutic agents for the treatment of clinical conditions, particularly migraine, requiring this activity. However, neither EP-A-0313397 nor WO-A-91/18897 discloses or suggests the imidazole, triazole and tetrazole derivatives provided by the present invention.

EP-A-0497512, published on 5 Aug. 1992, describes a class of substituted imidazole, triazole and tetrazole derivatives which are stated to be selective agonists of 5-$HT_1$-like receptors and hence to be of particular use in the treatment of migraine and associated conditions.

The present invention provides a compound of formula I, or a salt or prodrug thereof:

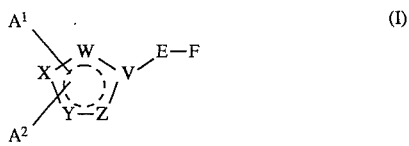

wherein the broken circle represents two non-adjacent double bonds in any position in the five-membered ring;

two, three or four of V, W, X, Y and Z represent nitrogen and the remainder represent carbon provided that, when two of V, W, X, Y and Z represent nitrogen and the remainder represent carbon, then the said nitrogen atoms are in non-adjacent positions within the five-membered ring;

$A^1$ represents hydrogen, hydrocarbon, a heterocyclic group, halogen, cyano, trifluoromethyl, —$OR^x$, —$SR^x$, —$NR^xR^y$, —$NR^xCOR^y$, —$NR^xCO_2R^y$, —$NR^xSO_2R^y$, or —$NR^zCTNR^xR^y$;

$A^2$ represents a non-bonded electron pair when four of V, W, X, Y and Z represent nitrogen and the other represents carbon; or, when two or three of V, W, X, Y and Z represent nitrogen and the remainder represent carbon, $A^2$ represents hydrogen, hydrocarbon, a heterocyclic group, halogen, cyano, trifluoromethyl, —$OR^x$, —$SR^x$, —$NR^xR^y$, —$NR^xC$-$OR^y$, —$NR^xCO_2R^y$, —$NR^xSO_2R^y$, or —$NR^zCTNR^xR^y$;

E represents a bond or a straight or branched alkylene chain containing from 1 to 4 carbon atoms;

F represents a group of formula

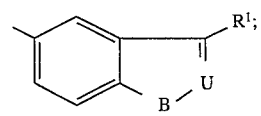

U represents nitrogen or C—$R^2$;
B represents oxygen, sulphur or N—$R^3$;
$R^1$ represents a group of formula (i), (ii) or (iii):

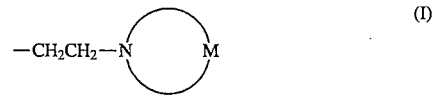

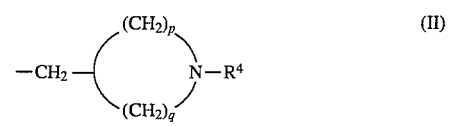

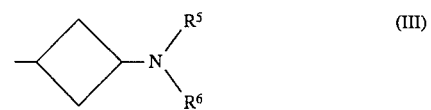

in which
M represents the residue of an azetidine, pyrrolidine or piperidine ring;
p is zero or 1 and q is an integer from 1 to 4,
$R^2$, $R^3$, $R^4$, $R^5$ and $R^6$ independently represent hydrogen or $C_{1-6}$ alkyl;
$R^x$ and $R^y$ independently represent hydrogen, hydrocarbon or a heterocyclic group, or $R^x$ and $R^y$ together represent a $C_{2-6}$ alkylene group;
$R^z$ represents hydrogen, hydrocarbon or a heterocyclic group;
T represents oxygen, sulphur or a group of formula =N.G; and
G represents hydrocarbon, a heterocyclic group or an electron-withdrawing group.

The present invention also provides compounds of formula I above wherein $R^1$ represents a group of formula (i) or (ii), and the remaining substituents are as defined above.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

A particular aryl group is phenyl.

Particular aryl($C_{1-6}$)alkyl groups include benzyl, phenethyl and phenylpropyl, Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl($C_{1-6}$)alkyl groups include pyridylmethyl and pyrazinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $NR^vR^w$, $-NR^vCOR^w$, $-NR^vCO_2R^w$, $-NR^vSO_2R^w$, $-CH_2NR^vSO_2R^w$, $-NHCONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

When the group G represents an electron-withdrawing group, this group is suitably cyano, nitro, $-COR^x$, $-CO_2R^x$ or $-SO_2R^x$, in which is as defined above.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. In addition, the compounds of formula I above wherein $R^1$ represents a group of formula (iii) may exist as discrete isomers in which the $-NR^5R^6$ group is either cis or trans to the other substituent on the cyclobutane ring. It is to be understood that all such isomers and mixtures thereof are encompassed within the scope of the present invention.

It will be appreciated that the imidazole, triazole and tetrazole rings of formula I can exist in a variety of isomeric forms having differing substitution patterns. These may suitably be represented by formulae IA to IT as follows:

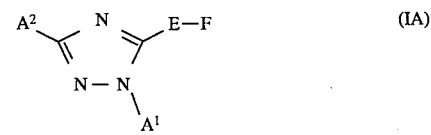
(IA)

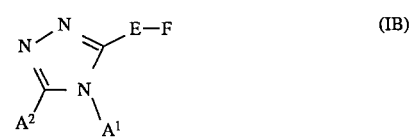
(IB)

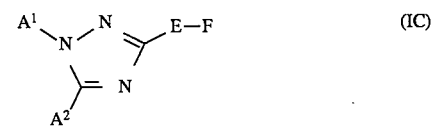
(IC)

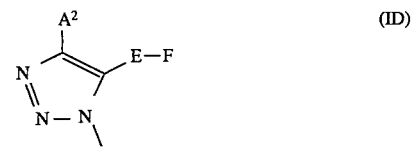
(ID)

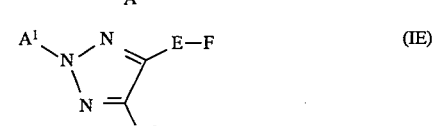
(IE)

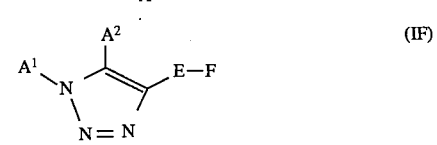
(IF)

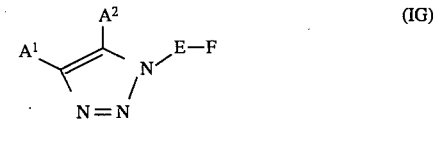
(IG)

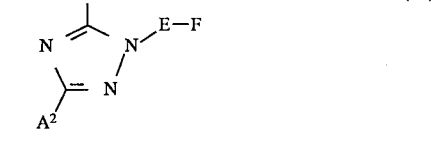
(IH)

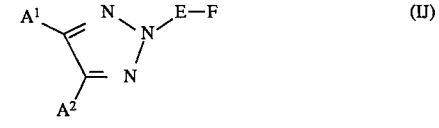
(IJ)

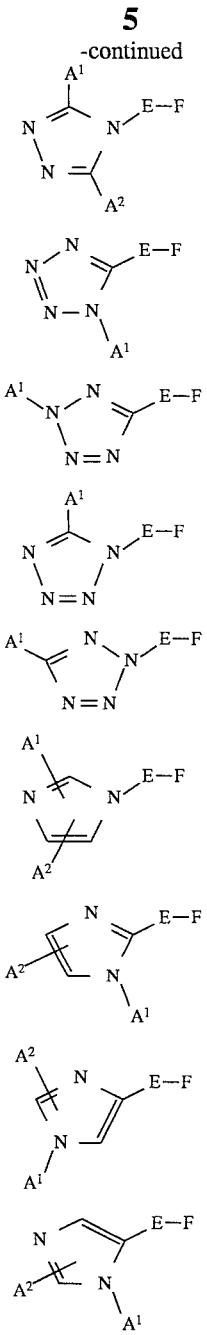

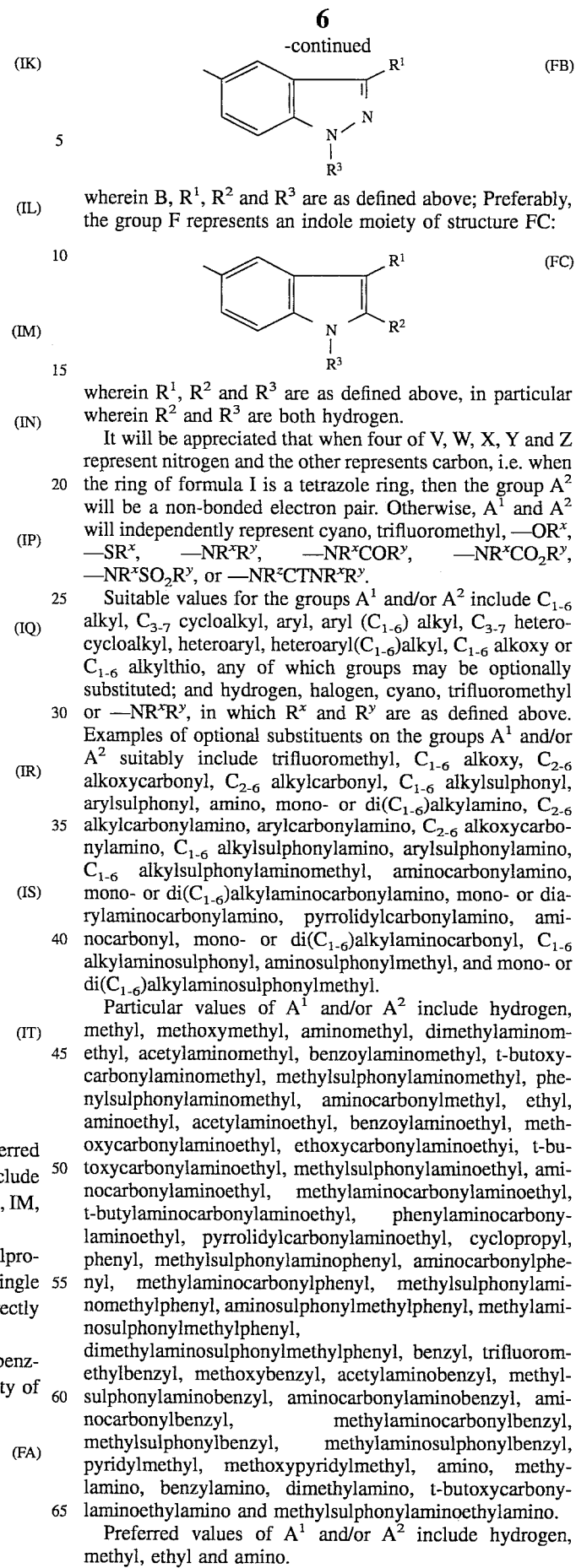

wherein $A^1$, $A^2$, E and F are as defined above. Preferred imidazole, triazole and tetrazole rings of formula I include the rings represented by formulae IA, IC, IG, IH, IK, IL, IM, IN, IP and IQ above, especially IH or IK.

The alkylene chain E may be, for example, 2-methylpropylene. Alternatively, the group E may represent a single bond such that the group F in formula I is attached directly to the five-membered heteroaromatic ring.

The group F is suitably an indole, benzofuran or benzthiophene moiety of formula FA, or an indazole moiety of formula FB:

wherein B, $R^1$, $R^2$ and $R^3$ are as defined above; Preferably, the group F represents an indole moiety of structure FC:

wherein $R^1$, $R^2$ and $R^3$ are as defined above, in particular wherein $R^2$ and $R^3$ are both hydrogen.

It will be appreciated that when four of V, W, X, Y and Z represent nitrogen and the other represents carbon, i.e. when the ring of formula I is a tetrazole ring, then the group $A^2$ will be a non-bonded electron pair. Otherwise, $A^1$ and $A^2$ will independently represent cyano, trifluoromethyl, —$OR^x$, —$SR^x$, —$NR^xR^y$, —$NR^xCOR^y$, —$NR^xCO_2R^y$, —$NR^xSO_2R^y$, or —$NR^zCTNR^xR^y$.

Suitable values for the groups $A^1$ and/or $A^2$ include $C_{1-6}$ alkyl, $C_{3-7}$ cycloalkyl, aryl, aryl ($C_{1-6}$) alkyl, $C_{3-7}$ heterocycloalkyl, heteroaryl, heteroaryl($C_{1-6}$)alkyl, $C_{1-6}$ alkoxy or $C_{1-6}$ alkylthio, any of which groups may be optionally substituted; and hydrogen, halogen, cyano, trifluoromethyl or —$NR^xR^y$, in which $R^x$ and $R^y$ are as defined above. Examples of optional substituents on the groups $A^1$ and/or $A^2$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of $A^1$ and/or $A^2$ include hydrogen, methyl, methoxymethyl, aminomethyl, dimethylaminomethyl, acetylaminomethyl, benzoylaminomethyl, t-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethylphenyl, aminosulphonylmethylphenyl, methylaminosulphonylmethylphenyl, dimethylaminosulphonylmethylphenyl, benzyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, pyridylmethyl, methoxypyridylmethyl, amino, methylamino, benzylamino, dimethylamino, t-butoxycarbonylaminoethylamino and methylsulphonylaminoethylamino.

Preferred values of $A^1$ and/or $A^2$ include hydrogen, methyl, ethyl and amino.

When R¹ represents a group of formula (ii), the resulting group is an azetidin-2-ylmethyl, azetidin-3-ylmethyl, pyrrolidin-2-ylmethyl, pyrrolidin-3-ylmethyl, piperidin-2-ylmethyl or piperidin-3-ylmethyl group, in particular an azetidin-3-ylmethyl or pyrrolidin-2-ylmethyl group, substituted on the ring nitrogen atom by the group R⁴.

In a particular embodiment, R¹ represents a group of formula (i) in which M represents the residue of an azetidine or pyrrolidine ring. Thus, R¹ suitably represents the azetidin-1-ylethyl or pyrrolidin-1-ylethyl moiety.

Preferred values for the groups $R^2$, $R^3$, $R^4$, $R^5$ and $R^6$ include hydrogen and methyl.

A particular sub-class of compounds according to the invention is represented by the compounds of formula II, and salts and prodrugs thereof:

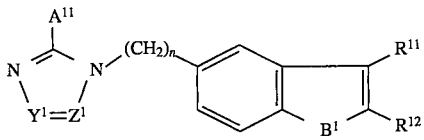

wherein $Y^1$ represents nitrogen or $A^{12}$—C;

$Z^1$ represents nitrogen or CH;

n is zero, 1, 2 or 3;

$B^1$ represents oxygen, sulphur or N—$R^{13}$;

$A^{11}$ and $A^{12}$ independently represent $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$)alkylamino, any of which groups may be optionally substituted; or hydrogen, halogen, cyano, trifluoromethyl or amino;

$R^{11}$ represents a group of formula (iv), (v), (vi), (vii) or (viii):

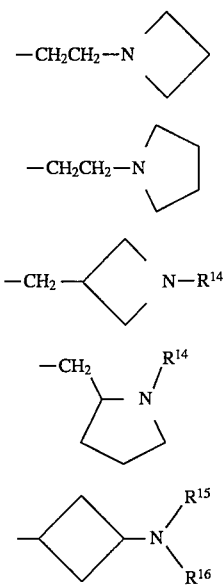

and $R^{12}$, $R^{13}$, $R^{14}$, $R^{15}$ and $R^{16}$ independently represent hydrogen or $C_{1-6}$ alkyl.

Examples of optional substituents on the groups $A^{11}$ and $A^{12}$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylamino-carbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkyl-aminosulphonylmethyl.

Particular values of $A^{11}$ and $A^{12}$ with respect to formula II include hydrogen, methyl, ethyl and amino, especially hydrogen.

Preferably, $R^{12}$ and $R^{13}$ each represents hydrogen. Preferably, $R^{14}$ is methyl.

Suitably, $R^{15}$ and $R^{16}$ are independently selected from hydrogen and methyl. Preferably, $R^{15}$ and $R^{16}$ are both methyl.

Specific compounds within the scope of the present invention include:

N-2-[5-(1,2,4-triazol-1-ylmethyl)-1H-indol-3-yl]ethylazetidine;

N-2-[5-(1,2,4-triazol-1-yl)-1H-indol-3-yl]ethylazetidine;

N-methyl-3-[5-(1,2,4-triazol-1-ylmethyl)-1H-indol-3-yl] methylazetidine;

N-methyl-2-[5-(1,2,4-triazol-1-ylmethyl)-1H-indol-3-yl] methylpyrrolidine;

(2R)-N-methyl-2-[5-(1,2,4-triazol-4-yl)-1H-indol-3-yl]methylpyrrolidine;

3-[cis-1-(N,N-dimethylamino)cyclobutan-3-yl]-5-(1,2,4-triazol-1-ylmethyl)-1H-indole;

3-[trans-1-(N,N-dimethylamino)cyclobutan-3-yl]-5-(1,2,4-triazol-1-ylmethyl)-1H-indole;

N-2-[5-(1,2,4-triazol-4-yl)-1H-indol-3-yl]ethylazetidine;

N-2-[5-(1,2,4-triazol-4-yl)-1H-indol-3yl]ethylpyrrolidine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of i to 4 times per day.

The 1,2,4-triazole compounds of this invention may be prepared by a process which comprises reacting a reactive derivative of a carboxylic acid of formula $R^a$—$CO_2H$ with a compound either of formula III or of formula IV, or a salt thereof:

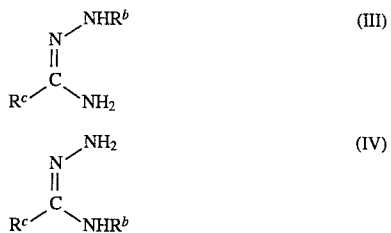

wherein one of $R^a$, $R^b$ and $R^c$ is a group of formula $A^1$, another is a group of formula $A^2$ and the third is a group of formula —E—F, as defined with reference to formula I above.

Suitable reactive derivatives of the acid $R^a$—$CO_2H$ include esters, for example $C_{1-4}$ alkyl esters; thioesters, for example pyridylthioesters; acid anhydrides, for example $(R^a$—$CO)_2O$; acid halides, for example acid chlorides; orthoesters; and primary, secondary and tertiary amides.

A preferred reactive derivative of the acid $R^a$—$CO_2H$ is the iminoether derivative of formula V:

where R is $C_{1-4}$ alkyl.

The reagent of formula III may be generated in situ in the reaction mixture. For example, the reaction may be effected by treating a compound of formula V above with an alkyl hydrazine, e.g. methyl hydrazine, followed by a suitable carboxylic acid such as formic acid.

The reaction is conveniently carried out by heating the reagents together, optionally in a solvent, for example tetrahydrofuran, dimethylformamide or a lower alkanol such as ethanol, propanol or isopropanol, at about 20° C. to 100° C. for about 1 to 6 hours.

Where $R^a$ is a group of formula —E—F and the group F is an indole moiety of structure FC as defined above, the reactive derivative of a carboxylic acid of formula $HO_2C$—E—F may be prepared by reacting a compound of formula VI:

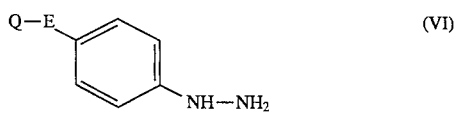

wherein Q represents a reactive carboxylate moiety, and E is as defined above; with a compound of formula VII or a carbonyl-protected form thereof:

wherein $R^2$ is as defined above and $R^{21}$ corresponds to the group $R^1$ as defined above or represents a protected derivative thereof; followed by removal of any protecting groups present; and subsequently, where required, N-alkylation by standard methods to introduce the moieties $R^3$ and/or $R^4$.

Suitable carbonyl-protected forms of the compounds of formula VII include the dimethyl acetal or ketal derivatives.

The reaction of compounds VI and VII may be carried out in a single step (Fischer indole synthesis) or by an initial non-cyclising step at a lower temperature to give a compound of formula VIII:

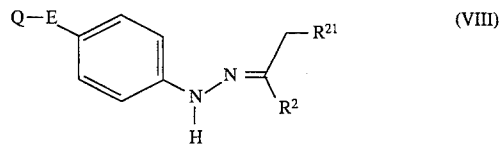

wherein Q, E, $R^2$ and $R^{21}$ are as defined above; followed by cyclisation using a suitable reagent, such as a polyphosphate ester, to give a compound of formula Q—E—F.

The hydrazines of formula VI may be prepared from the corresponding anilines of formula IX:

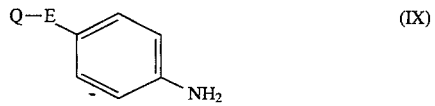

wherein Q and E are as defined above; by diazotisation followed by reduction. Diazotisation is typically carried out using sodium nitrite/conc. HCl and the resulting diazo product reduced in situ using, for example, tin(II) chloride/conc. HCl, sodium sulphite/conc. HCl, or sodium sulphite/conc. $H_2SO_4$.

The anilines of formula IX may be prepared by reduction of the corresponding nitro compounds of formula X:

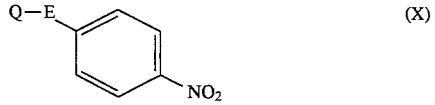

wherein Q and E are as defined above; typically by transfer hydrogenation using a hydrogenation catalyst such as palladium on charcoal in the presence of a hydrogen donor such as ammonium formate, or alternatively by conventional catalytic hydrogenation or using tin(II) chloride.

Where they are not commercially available, the nitro compounds of formula X may be synthesized by standard methods well known to those skilled in the art.

Where $R^a$ is a group of formula —E—F and the group F is an indazole moiety of structure FB as defined above, the reactive derivative of a carboxylic acid of formula $HO_2C$—E—F may be prepared by the cyclisation of a compound of formula XI:

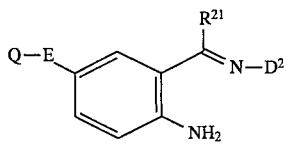

wherein Q, E and $R^{21}$ are as defined above and $D^2$ represents a readily displaceable group; followed by removal of any protecting groups present; and subsequently, where required, N-alkylation by standard methods to introduce the moieties $R^3$ and/or $R^4$.

The cyclisation of compound XI is conveniently achieved in a suitable organic solvent at an elevated temperature, for example in a mixture of m-xylene and 2,6-lutidine at a temperature in the region of 140° C.

The readily displaceable group $D^2$ in the compounds of formula XI suitably represents a $C_{1-4}$ alkanoyloxy group, preferably acetoxy. Where $D^2$ in the desired compound of formula XI represents acetoxy, this compound may be conveniently prepared by treating a carbonyl compound of formula XII:

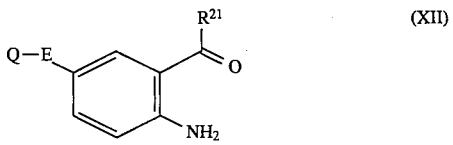

wherein Q, E and $R^{21}$ are as defined above; or a protected derivative thereof; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivative of the intermediate of formula XII may be conveniently prepared by ozonolysis of an indole derivative of formula XIII:

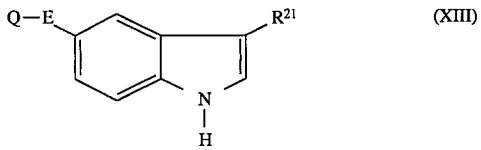

wherein Q, E and $R^{21}$ are as defined above; followed by a reductive work-up, advantageously using dimethylsulphide.

The indole derivative of formula XIII may be prepared by methods analogous to those described in the accompanying Examples, or by procedures well known from the art.

In an alternative process, the triazole compounds according to the invention may be prepared by a method which comprises reacting a compound of formula XIV:

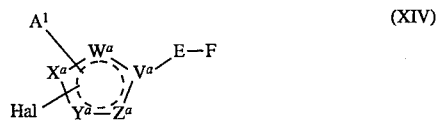

wherein $A^1$, E and F are as defined above, Hal represents halogen, and two of $V^a$, $W^a$, $X^a$, $Y^a$ and $Z^a$, to one of which the group Hal is attached, represent carbon and the remainder represent nitrogen; with a reagent which provides an anion $^-A^2$, where $A^2$ is as previously defined.

Reagents which may provide the anion $^-A^2$ include Grignard reagents $A^2MgHal$ (where Hal=halogen); organocuprate reagents such as $LiA^2_2Cu$; organolithium reagents $A^2Li$; or compounds which stabilise the anion by means of an adjacent activating group such as an ester or enolisable ketone function. In this case, the adjacent ester or ketone function may be retained after the process is complete, or may be removed. For example, an ester moiety may be hydrolysed and decarboxylated.

The 1,2,3-triazole compounds according to the present invention may be prepared by a process which comprises the cycloaddition of an alkyne of formula $R^a$—C≡C—$R^b$ with an azide of formula $R^c$—$N_3$, where $R^a$ $R^b$ and $R^c$ are as defined above.

The cycloaddition reaction may be conveniently effected in a suitable solvent such as tetrahydrofuran, ideally by heating in an autoclave for 8 hours.

The tetrazole compounds in accordance with the invention may be prepared by a process which comprises the cycloaddition of a nitrile of formula N≡C—$R^d$ with an azide of formula $R^e$—$N_3$, where one of $R^d$ and $R^e$ represents a group of formula $A^1$ and the other is a group of formula —E—F, as defined previously.

The cycloaddition reaction is conveniently effected by heating the reactants together at an elevated temperature, e.g. a temperature in the region of 150° C., in a suitable solvent such as N-methylpyrrolid-2-one, advantageously in the presence of triethylamine hydrochloride. The product obtained from the cycloaddition reaction will generally be a mixture of isomers substituted by the $A^1$ group at positions 1 and 2 of the tetrazole ring, corresponding to structures IL and IM respectively as defined above. These isomers may conveniently be separated using conventional techniques such as chromatography.

In an alternative process, the tetrazole compounds of the invention may be prepared by a method which comprises reacting a compound of formula $R^e$—L with a tetrazole derivative of formula XV:

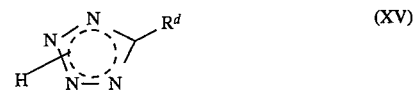

wherein one of $R^d$ and $R^e$ represents a group of formula $A^1$ and the other is a group of formula —E—F, as defined above, and L represents a suitable leaving group; in the presence of a base such as triethylamine.

The leaving group L suitably represents halogen, e.g. bromine or iodine, or a sulphonate derivative such as tosylate or mesylate.

The reaction is conveniently carried out in a suitable organic solvent, e.g. acetonitrile, at room temperature.

The tetrazole derivatives of formula XV may be prepared by cycloaddition of a nitrile of formula N≡C—$R^d$ with sodium azide, advantageously under the conditions described above for the reaction between the nitrile N≡C—$R^d$ and the azide $R^e$—$N_3$; followed by acidification with a mineral acid such as hydrochloric acid.

In a further process, the compounds according to the invention wherein the group F is an indole moiety of structure FC as defined above may be prepared by a method which comprises reacting a compound of formula XVI:

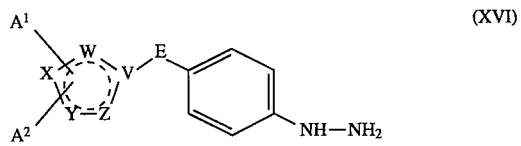

wherein V, W, X, Y, Z, $A^1$, $A^2$ and E are as defined above; with a compound of formula VII as defined above, or a carbonyl-protected form thereof, e.g. the dimethyl acetal or ketal; followed by removal of any protecting groups present;

and subsequently, where required, N-alkylation by standard methods to introduce the moieties $R^3$ and/or $R^4$.

As with that between compounds VI and VII, the reaction between compounds XVI and VII may be carried out in a single step (Fischer indole synthesis) or by an initial non-cyclising step at a lower temperature to give a compound of formula XVII:

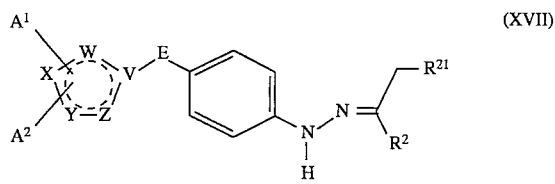
(XVII)

wherein V, W, X, Y, Z, $A^1$, $A^2$, E, $R^2$ and $R^{21}$ are as defined above; followed by cyclisation using a suitable reagent, e.g. a polyphosphate ester.

The hydrazines of formula XVI may be prepared from the corresponding anilines of formula XVIII:

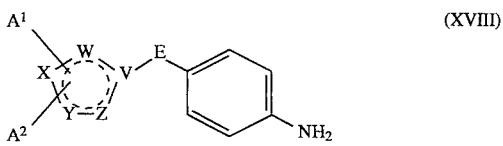
(XVIII)

wherein V, W, X, Y, Z, $A^1$, $A^2$ and E are as defined above; by methods analogous to those described above with reference to the compounds of formula IX.

The anilines of formula XVIII may be prepared from the corresponding nitro compounds of formula XIX:

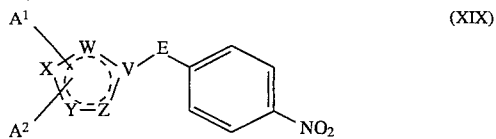
(XIX)

wherein V, W, X, Y, Z, $A^1$, $A^2$ and E are as defined above; by methods analogous to those described above with reference to the compounds of formula X.

The nitro compounds of formula XIX may be prepared by a variety of methods which will be readily apparent to those skilled in the art. For example, where V represents a nitrogen atom, the relevant compounds of formula XIX may be prepared by reacting the anion of a compound of formula XX with a compound of formula XXI:

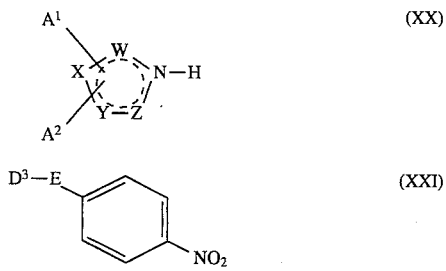
(XX)

(XXI)

wherein W, X, Y, Z, $A^1$, $A^2$ and E are as defined above, and $D^3$ represents a readily displaceable group.

Where compound XX is a triazole or tetrazole derivative, the anion thereof may be generated by carrying out the reaction in a base such as triethylamine. Where compound XX is an imidazole derivative, the anion thereof may conveniently be generated if the reaction is carried out in the presence of sodium hydride using N,N-dimethylformamide as solvent. Where salts of the compounds of formula XX are commercially available, e.g. the sodium salt of 1,2,4-triazole, these are advantageously utilised in N,N-dimethylformamide solution in place of the compounds of formula XX themselves, with no requirement in this instance for additional base to be present in the reaction mixture.

The readily displaceable group $D^3$ in the compounds of formula XXI is suitably a halogen atom, preferably bromine; except when the moiety $D^3$ is attached directly to the aromatic ring, i.e. when E represents a bond, in which case $D^3$ is preferably fluorine.

In an alternative approach, the compounds of formula XIX wherein the five-membered heteroaromatic ring is a 1,2,4-triazol-1-yl moiety and $A^1$ and $A^2$ are both hydrogen may be prepared by reacting 4-amino-1,2,4-triazole with a compound of formula XXI as defined above, followed by deamination of the resulting 1-substituted 4-amino- 4H-1, 2,4-triazolium salt by treatment with nitrous acid and subsequent neutralisation. This transformation, which may be accomplished in two separate steps or advantageously as a "one-pot" procedure with both steps combined, is conveniently effected using reaction conditions analogous to those described in J. Org. Chem., 1989, 54, 731.

Where they are not commercially available, the nitro compounds of formula XXI above may be prepared by procedures analogous to those described in the accompanying Examples, or by methods well known from the art.

In an alternative approach to the 1,2,4-triazole derivatives, the nitro compounds of formula XIX may be prepared from those of formula X above by appropriate modification of the moiety Q using, for example, methods analogous to those described above with reference to the compounds of formulae III and IV. Thus, for example, since Q in the compounds of formula X represents a reactive carboxylate moiety, the compounds of formula XIX may be prepared therefrom by reaction with a compound of formula $A^2$—C($=$NNHA$^1$)NH$_2$ or $A^2$—C($=$NNH$_2$)NHA$^1$.

Following a further representative pathway, the aniline derivatives of formula XVIII wherein the five-membered heteroaromatic ring is a 1,2,4-triazol-4-yl moiety, E is a bond and $A^1$ and $A^2$ are both hydrogen may be prepared by reacting the hydrazine derivative of formula XXII with the acetanilide of formula XXIII:

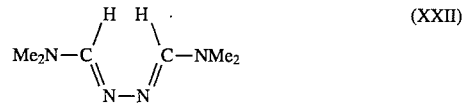
(XXII)

(XXIII)

followed by removal of the N-acetyl protecting group.

The reaction between compounds XXII and XXIII is conveniently effected in refluxing toluene, advantageously in the presence of a catalytic quantity of p-toluenesulphonic acid. Subsequent removal of the N-acetyl protecting group is typically effected in hot aqueous 5N hydrochloric acid.

The hydrazine derivative of formula XXII can be prepared from N,N'-diformylhydrazine by reaction with thionyl chloride/N,N-dimethylformamide, as reported in J. Chem. Soc. (C), 1967, 1664, and subsequent treatment with sodium methoxide in methanol.

The acetanilide of formula XXIII may be prepared by reduction of the corresponding nitro compound of formula XXIV:

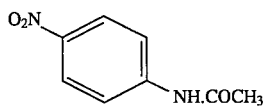 (XXIV)

typically by transfer hydrogenation using a hydrogenation catalyst in the presence of a hydrogen donor such as ammonium formate, or alternatively by conventional catalytic hydrogenation or using tin(II) chloride.

The nitro compound of formula XXIV is commercially available from the Aldrich Chemical Company Ltd., Gillingham, United Kingdom.

In a still further process, the compounds according to the invention wherein the group F is an indazole moiety of structure FB as defined above may be prepared by a method which comprises cyclising a compound of formula XXV:

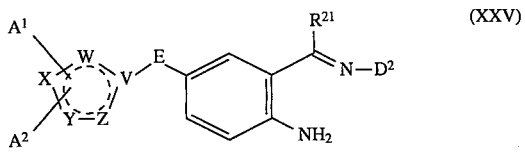 (XXV)

wherein V, W, X, Y, Z, $A^1$, $A^2$, E, $R^{21}$ and $D^2$ are as defined above; followed by removal of any protecting groups present; and subsequently, where required, N-alkylation by standard methods to introduce the moieties $R^3$ and/or $R^4$.

As with the cyclisation of compound XI, that of compound XXV is conveniently achieved in a suitable organic solvent at an elevated temperature, for example in a mixture of m-xylene and 2,6-lutidine at a temperature in the region of 140° C.

The compounds of formula XXV may, for example, be prepared from the corresponding compound of formula XXVI:

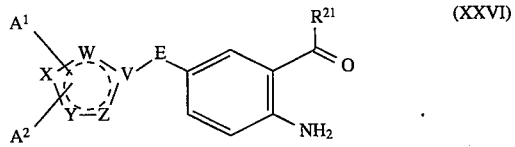 (XXVI)

wherein V, W, X, Y, Z, $A^1$, $A^2$, E and $R^{21}$ are as defined above; or a protected derivative thereof; which in turn may be prepared from the corresponding compound of formula XXVII:

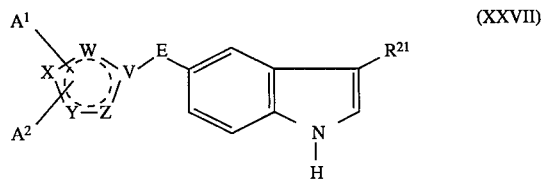 (XXVII)

wherein V, W, X, Y, Z, $A^1$, $A^2$, E and $R^{21}$ are as defined above; using methods analogous to those described above with reference to the compounds of formulae XII and XIII. Thus, for example, since Q in the compounds of formula XIII represents a reactive carboxylate moiety, the 1,2,4-triazole derivatives of formula XXVII may be prepared therefrom by reaction with a compound of formula $A^2$—C(=NNHA$^1$)NH$_2$ or $A^2$—C(=NNH$_2$)NHA$^1$.

In a yet further process, the compounds according to the invention wherein the group F is a benzofuran or benzthiophene moiety may be prepared by a method which comprises cyclising a compound of formula XXVIII:

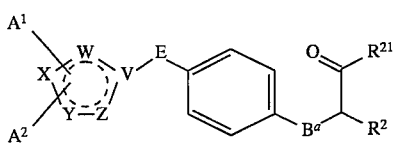 (XXVIII)

wherein V, W, X, Y, Z, $A^1$, $A^2$, E, $R^2$ and $R^{21}$ are as defined above, and $B^a$ represents oxygen or sulphur; followed by removal of any protecting groups present; and subsequently, where required, N-alkylation by standard methods to introduce the moiety $R^4$.

The cyclisation is conveniently effected by using polyphosphoric acid or a polyphosphate ester, advantageously at an elevated temperature.

The compounds of formula XXVIII may be prepared by reacting a compound of formula XXIX with a compound of formula XXX:

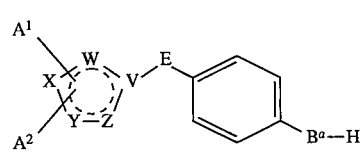 (XXIX)

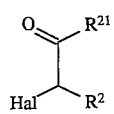 (XXX)

wherein V, W, X, Y, Z, $A^1$, $A^2$, E, $B^a$, $R^2$ and $R^{21}$ are as defined above, and Hal represents halogen.

The reaction is conveniently effected in the presence of a base such as sodium hydroxide.

The hydroxy and mercapto derivatives of formula XXIX may be prepared by a variety of methods which will be readily apparent to those skilled in the art. In one such method, the anion of a compound of formula XX as defined above is reacted with a compound of formula XXXI:

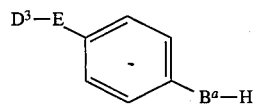 (XXXI)

wherein $D^3$, E and $B^a$ are as defined above; to afford an intermediate of formula XXIX wherein V is nitrogen.

The compounds of formula XXX and XXXI, where they are not commercially available, may be prepared by standard procedures well known in the art.

The intermediates of formula VII wherein $R^{21}$ represents a group of formula (i) as defined above with reference to $R^1$, or the carbonyl-protected forms thereof, may conveniently be prepared by reacting a compound of formula XXXII, or a carbonyl-protected form thereof, with a compound of formula XXXIII:

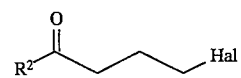 (XXXII)

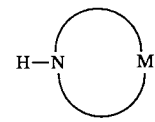 (XXXIII)

wherein $R^2$ and M are as defined above; and Hal represents halogen, especially chlorine. The reaction is suitably carried out in the presence of a base such as potassium carbonate, typically in a solvent such as N,N-dimethylformamide.

The preparation of a typical intermediate of formula VII, wherein $R^{21}$ represents an azetidin-3-ylmethyl moiety protected on the ring nitrogen atom by a t-butoxycarbonyl (BOC) group, is illustrated by the following reaction scheme:

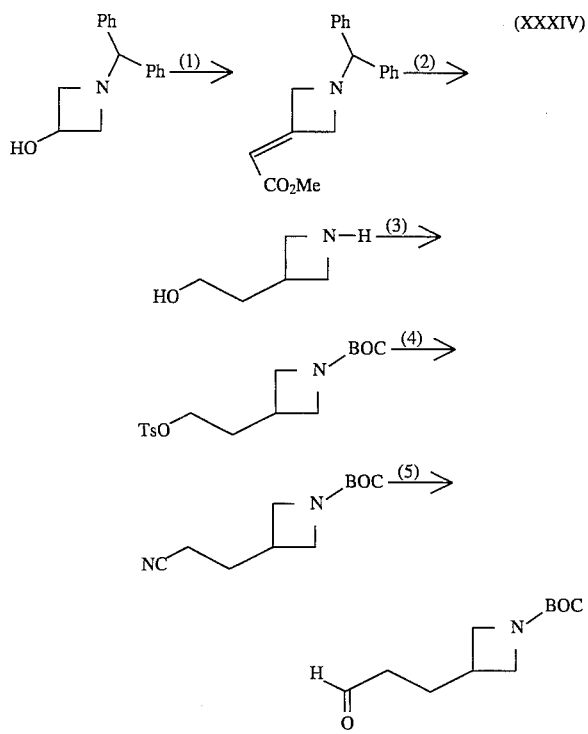

The starting compound XXXIV is known from *J. Chem. Soc., Chem Commun.*, 1968, 93. Step 1 of the reaction scheme comprises oxidation of the hydroxy group of compound XXXI to a carbonyl group using pyridine.SO$_3$ in dimethyl sulphoxide (DMSO) and triethylamine; followed by reaction of the resulting azetidinone derivative with the Horner-Emmons reagent MeO$_2$C.CH$_2$.PO(OEt)$_2$ in the presence of sodium hydride, using tetrahydrofuran (THF) as the solvent. In Step 2, the double bond of the azetidine olefin ester is hydrogenated over palladium-charcoal in methanol; the methyl ester group is then reduced to hydroxymethyl by treatment with lithium aluminium hydride in THF; and the diphenylmethyl protecting group is in turn removed by treatment with palladium hydroxide on charcoal, with methanol serving as the solvent. Step 3 involves protection of the azetidine nitrogen as the N-t-butoxycarbonyl (N-BOC) carbamate derivative; followed by conversion of the primary hydroxy group to tosyloxy by reaction with p-toluenesulphonyl chloride (tosyl chloride, TsCl) in pyridine/dichloromethane. Displacement of the tosyloxy group by cyanide ion in Step 4 is followed in Step 5 by reduction of the resulting cyano compound to the corresponding aldehyde derivative using diisobutylaluminium hydride (DIBAL-H) in THF, with an ammonium chloride work-up.

The preparation of a further typical intermediate of formula VII, in which R$^{21}$ represents a pyrrolidin-2-ylmethyl moiety protected on the ring nitrogen atom by a BOC group, is illustrated by the following reaction scheme:

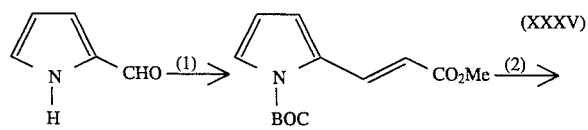

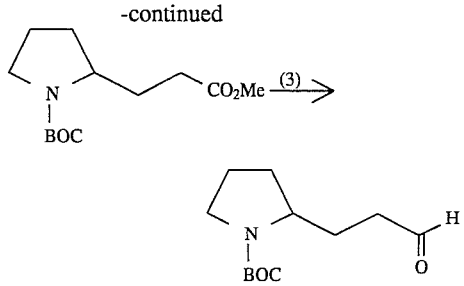

The starting compound XXXV is commercially available from Aldrich Chemical Company Ltd., Gillingham, U.K. Step 1 of the reaction scheme involves protection of the pyrrole nitrogen as the N-t-butoxycarbonyl (N-BOC) carbamate derivative; followed by reaction of the formyl moiety in the 2-position with the Horner-Emmons reagent MeO$_2$C.CH$_2$.PO(OEt)$_2$ in the presence of sodium hydride, using THF as the solvent. In Step 2, the pyrrole and exocyclic double bonds are hydrogenated over platinum oxide in acetic acid. This is followed in Step 3 by partial reduction of the side-chain methyl ester group to an aldehyde moiety using DIBAL-H in THF at –80° C.

In a variant of the reaction scheme described immediately above, a chiral intermediate of formula VII, in which R$^{21}$ represents a pyrrolidin-2-ylmethyl moiety having a chiral centre at the 2-position and protected on the ring nitrogen atom by a BOC group, is illustrated by the following reaction scheme:

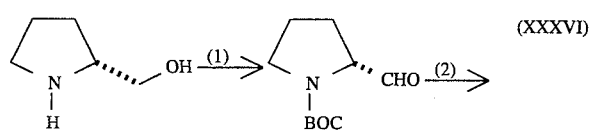

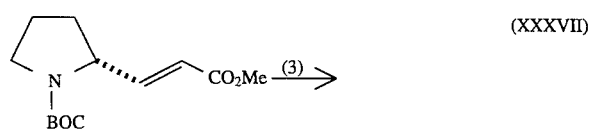

The starting compound XXXVI, D-prolinol, is commercially available from Aldrich Chemical Company Ltd., Gillingham, U.K. Step 1 of the reaction scheme involves protection of the pyrrolidine nitrogen as the N-BOC derivative, typically using BOC anhydride in dichloromethane; followed by Swern oxidation (oxalyl chloride/dimethyl sulphoxide/dichloromethane/–78° C., then triethylamine) of the terminal hydroxy group to an aldehyde moiety. Step 2 involves reaction with the Horner-Emmons reagent MeO$_2$C.CH$_2$.PO(OEt)$_2$ in the presence of sodium hydride, using THF as the solvent. In Step 3 the side-chain double bond is reduced, conveniently by catalytic hydrogenation over palladium-charcoal in aqueous methanol; and the methyl ester moiety is then partially reduced to an aldehyde functionality using DIBAL-H in THF at –78° C., to give the desired product of formula XXXVII.

As will be appreciated, the compound corresponding to compound XXXVII, but having the opposite stereochemistry at the 2-position of the pyrrolidine ring, is readily obtainable, using an identical sequence of steps, from L-prolinol (i.e. the opposite antipode of compound XXXVI), which is also commercially available from Aldrich Chemical Company Ltd.

The preparation of a still further typical intermediate of formula VII, in which $R^{21}$ represents a BOC-protected 3-aminocyclobutan-1-yl moiety, is illustrated by the following reaction scheme:

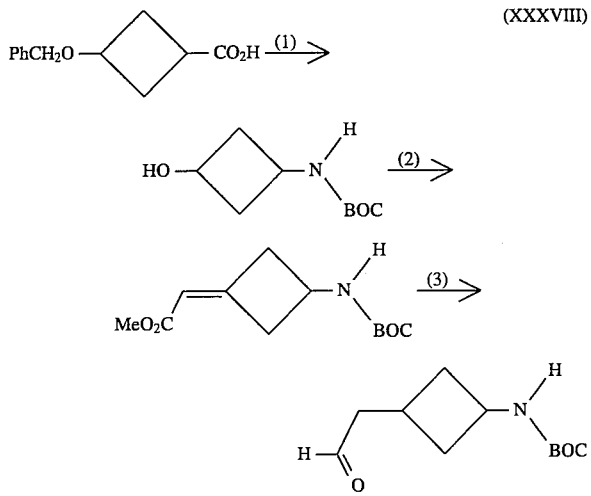

(XXXVIII)

The starting compound XXXVIII is known from *Coll. Czech. Chem. Commun.*, 1981, 47, 2440. Step 1 of the reaction scheme involves treatment thereof with diphenylphosphoryl azide and 2-methyl-2-propanol in the presence of triethylamine under reflux, to convert the carboxylic acid moiety into an —NHBOC group; followed by removal of the O-benzyl protecting group by catalytic hydrogenation over palladium/carbon. In Step 2, the hydroxy group is oxidised to keto using pyridinium chlorochromate, or N-methylmorpholine N-oxide in the presence of tetrapropylammoniumperruthenate and molecular sieve; and the resulting keto group is in turn reacted with the Horner-Emmons reagent $MeO_2C.CH_2.PO(OEt)_2$ in the presence of potassium bis(trimethylsilyl)amide. Step 3 comprises reduction of the exocyclic double bond, conveniently by catalytic hydrogenation over palladium on carbon; and then partial reduction of the side-chain methyl ester group to an aldehyde moiety using DIBAL-H in toluene at about −80° C.

It will be understood that any compound of formula I initially obtained from any of the above processes may, where appropriate, subsequently be elaborated into a further compound of formula I by techniques known from the art. Indeed, as will be appreciated, the compound of formula XV above in which $R^d$ is a group of formula —E—F is itself a compound of formula I in which $A^1$ is hydrogen and $A^2$ represents a non-bonded electron pair. In particular, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile. Similarly, a compound of formula I wherein $R^4$, $R^5$ or $R^6$ represents hydrogen initially obtained may be converted into a compound of formula I wherein $R^4$, $R^5$ or $R^6$ is other than hydrogen, for example by conventional N-alkylation techniques, e.g. by treatment with the appropriate aldehyde in the presence of a reducing agent such as sodium cyanoborohydride.

Where the above-described processes for the preparation of the compounds according to the invention give rise to mixtures of stereoisomers, these isomers may be separated by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The ability of test compounds to bind to 5-HT$_1$-like receptors was measured in membranes prepared from pig caudate using the procedure described in *J. Neurosci.*, 1987, 7, 894. Binding was determined using 2 nM 5-hydroxytryptamine creatinine sulphate, 5-[1,2-$^3$H(N)] as a radioligand. Cyanopindolol (100 nM) and mesulergine (100 nM) were included in the assay to block out 5-HT$_{1A}$ and 5-HT$_{1C}$ binding sites respectively. The concentration of the compounds of the accompanying Examples required to displace 50% of the specific binding (IC$_{50}$) is below 1 μM in each case.

The activity of test compounds as agonists of the 5-HT$_1$-like receptor was measured in terms of their ability to mediate contraction of the saphenous vein of New Zealand White rabbits, using the procedure described in *Arch. Pharm.*, 1990, 342, 111. Agonist potencies were calculated as $-\log_{10}EC_{50}$ (pEC$_{50}$) values, from plots of percentage 5-HT (1 μM) response against the concentration of the agonist. The compounds of the accompanying Examples were found to possess pEC$_{50}$ values in this assay of not less than 5.0 in each case.

EXAMPLE 1

N-2-[5-(1,2,4-Triazol-1-ylmethyl)-1H-indol-3-yl]ethyl azetidine. Hydrogen Oxalate.

INTERMEDIATE 1

4-(1-Azetidinyl)butanal dimethylacetal

A mixture of azetidine (2.0 g, 35.0 mmol), 4-chlorobutanal dimethylacetal (5.88 g, 39.0 mmol) and $K_2CO_3$ (5.38 g, 39.0 mmol), in anhydrous DMF (100ml), was stirred at room temperature for 72 h. Water (50 ml) was added and the mixture extracted with EtOAc (3×150 ml). The combined extracts were washed with $H_2O$ (3×50ml), dried ($Na_2SO_4$) and evaporated. The crude product was purified by distillation (1.2 g). δ (360 MHz, CDCl$_3$) 1.35–1.42 (2H, m, CH$_2$), 1.57–1.64 (2H, m, CH$_2$), 2.00–2.40 (2H, m, CH$_2$), 2.36 (2H, t, J=9.0 Hz, CH$_2$), 3.15 (4H, m, t, J=7.0 Hz, 2 of CH$_2$), 3.33 (6H, s, 2 of OMe), 4.35 (1H, t, J=5.7 Hz, CH).

INTERMEDIATE 2

1-(4-Hydrazinophenyl)methyl-1,2,4-triazole 1. 1-(4-Nitrophenyl)methyl-1,2,4-triazole 4-Nitrobenzylbromide (21.6 g, 0.1 mol) was added to a rapidly stirred suspension of 1,2,4-triazole sodium salt (9.1 g, 0.1 mmol) in anhydrous DMF (100 ml) and the mixture stirred at room temperature for 16 h. Ethyl acetate (400 ml) was added followed by water (250 ml) and the layers separated. The organic phase was washed with water (3×250 ml), dried (MgSO$_4$) and evaporated. The residue was chromategraphed on silica gel eluting with ethyl acetate to give the title-product (10.6 g, 52%); m.p. 98°–100° C. δ (360 MHz, CDCl$_3$) 5.47 (2H,s,CH$_2$), 7.40 (2H, d, J=9 Hz, Ar—H), 8.02 (1H,s,Ar—H), 8.18 (1H, s, Ar—H), 8.23 (2H, d, J=9 Hz, Ar—H).

2. 1-(4-Aminophenyl)methyl-1,2,4-triazole. Hydrochloride

A solution of 1-(4-nitrophenyl)methyl-1,2,4-triazole (10.0 g, 49 mmol) in ethanol (50 ml), ethyl acetate (50 ml), 5N HCl (10 ml) and water (10 ml) was hydrogenated over 10% Pd/C(1.0 g) at 40 psi, in a Parr apparatus, until an uptake of 188 psi, had been observed (approx 10 mins). The catalyst was removed by filtration through hyflo and the solvent removed under vacuum. The residue was azeotroped with ethanol (×2) to give the title-amine hydrochloride (10.6 g, 100%). δ (360 MHz, D$_2$O) 5.53 (2H, s, CH$_2$), 7.37–7.48 (4H, m, Ar—H), 8.12 (1H, s, Ar—H), 8.66 (1H, s, Ar—H).

3. 1-(4-Hydrazinophenyl)methyl-1,2,4-triazole

A solution of sodium nitrite (3.28 g, 48 mmol) in water (20 ml) was added to a solution of the preceding amine hydrochloride (10.0 g, 48 mmol), in concentrated HCl (40 ml), at such a rate that the temperature did not exceed −10° C. After addition was complete the solution was stirred at 0° C. for 0.25 h and then added portionwise to a rapidly stirred solution of SnCl$_2$.2H$_2$O (40 g) in concentrated HCl (40 ml). The solution was warmed to room temperature and basified with 20% aqueous NaOH solution. The solution was extracted with ethyl acetate (3×250 ml) and the combined extracts dried (MgSO$_4$) and filtered through hyflo. The solution was evaporated to dryness to give the desired hydrazine (5.0 g, 56%) m.p. 109°–112° C. δ (360 MHz, D$_6$—DMSO) 3.93 (2H, br s, NH$_2$), 5.20 (2H, s, CH$_2$), 6.73 (2H, d, J=8 Hz, Ar—H), 7.08 (2H, d, J=8 Hz, Ar—H), 7.92 (1H, s, Ar—H), 8.57 (1H, s, Ar—H).

N-2-[5-(1,2,4,-Triazol-1-ylmethyl)-1H-indol-3-yl)ethylazetid ine. Hydrogen Oxalate. Hemihvdrate.

A solution of 1-(4-hydrazinophenyl)methyl-1,2,4-triazole (0.92 g, 4.1 mmol) and 4-(1-azetidinyl)butanal dimethylacetal (0.65 g, 3.8 mmol), in 4% H$_2$SO$_4$ (30 ml), was refluxed for 4.5 h. The solution was cooled to room temperature, basified with K$_2$CO$_3$ and extracted with EtOAc (4×100 ml). The combined extracts were dried (Na$_2$SO$_4$) and evaporated and the residue chromatographed on silica-gel eluting with CH$_2$Cl$_2$/MeOH/NH$_3$ (40:8:1) to give the title-indole. The hydrogen oxalate hemihydrate salt was prepared (30 mg); m.p. 128°–129° C. Found: C, 57.28, H, 5.95; N, 18.05. C$_{16}$H$_{19}$N$_5$.C$_2$H$_2$O$_4$.0.45 H$_2$O requires C, 56.97; H, 5.82; N,18.45%). δ (360 MHz, D$_2$O) 2.30–2.54 (2H, m, CH$_2$), 3.07 (2H, t, J=7.0 Hz, CH$_2$), 3.52 (2H, t, J=7.0 Hz, CH$_2$), 3.94–4.13 (4H, m, 2 of CH$_2$), 5.51 (2H, s, CH$_2$), 7.20 (1H, dd, J=1.5 and 8.4 Hz, Ar—H), 7.30 (1H, s, Ar—H), 7.51 (1H, d, J=8.4 Hz, Ar—H), 7.62 (1H, s, Ar—H), 8.05 (1H, s, Ar—H), 8.56 (1H, s, Ar—H).

EXAMPLE 2

N-2-[5-(1,2,4-Triazol-1-yl)-1H-indol-3-yl]ethylazetidine. Bisoxalate

INTERMEDIATE 3

4-(1,2,4-Triazol-1-yl)phenylhydrazine. Hydrochloride 1. 4-(1,2,4-Triazol-1-yl)nitrobenzene 1,2,4-Triazole sodium derivative (90%) (17.74 g, 0.18 mol) and 1-fluoro-4-nitrobenzene (25 g, 0.18 mol), in DMF, (150 ml) was stirred at room temperature for 4 days. Water (300 ml) and ethyl acetate (500 ml) were added and the mixture extracted. The organic layer was separated, washed with water (3×300 ml), dried (MgSO$_4$) and evaporated to give the desired product (24.8 g); δ (360 MHz, CDCl$_3$) 7.92 (2H, d, J=9.1 Hz, Ar—H); 8.17 (1H, s, Ar—H); 8.40.(2H, d, J=9.1 Hz, Ar—H); 8.48 (1H, s, Ar—H).

2. 4-(1,2,4-Triazol-1-yl)phenylhydrazine. Hydrochloride

Prepared from 4-(1,2,4-triazol-1yl)nitrobenzene using the procedure described for the preparation of Intermediate 2. δ (360 MHz, CDCl$_3$) 3.66 (2H, br s, NH$_2$), 5.36 (1H, br s, NH), 6.88–6.96 and 7.44–7.50 (both 2H, both m, At—H), 8.06 (1H, s, Ar—H), 8.42 (1H, s, Ar—H).

N-2-[5-(1,2,4-Triazol-1-yl)-1H-indol-3-yl]ethylazetidine. Bisoxalate

A solution of 4-(1,2,4-triazol-1-yl)phenylhydrazine hydrochloride (0.85 g, 4.0 mmol) and 4-(1-azetidinyl)butanal dimethylacetal (0.63 g, 3.6 mmol), in 4% H$_2$SO$_4$ (30 ml), was heated at reflux for 5 h. The solution was cooled to room temperature, basified with saturated. K$_2$CO$_3$ solution and extracted with EtOAc (4×70 ml). The combined extracts were dried (Na$_2$SO$_4$) and evaporated and the crude product chromategraphed on silica-gel eluting with CH$_2$Cl$_2$/MeOH$_3$ (80:8:1) to give the title-product. The bisoxalate salt was prepared (0.16 g), m.p. 164–°165° C. Found: C, 48.26; H, 4.65, N, 14.09. C$_{15}$H$_{17}$N$_5$.2.55 (C$_2$H$_2$O$_4$) requires C, 48.58; H, 4.48; N, 14.09%. δ (360 MHz, D$_2$O) 2.32–2.58 (2H, m, CH$_2$), 3.11 (2H, t, J=7.0 Hz, CH$_2$), 3.56 (2H, t, J=7.0 Hz, CH$_2$), 4.00–4.17 (2H, m, CH$_2$), 7.40 (1H, s, Ar—H), 7.49 (1H, dd, J=2.0 and 8.7 Hz, Ar—H), 7.64 (1H, d, J=8.7 Hz, Ar—H), 7.90 (1H, d, J=2.0 Hz, Ar—H), 8.47 (1H, s, Ar—H), 9.18 (1H, s, Ar—H).

EXAMPLE 3

N-Methyl-3-F5-(1,2,4-triazol-1-ylmethyl)-1H-indol,3-yl]methylazetidine. 0.65 Oxalate

INTERMEDIATE 4

N-tert-Butyloxycarbonyl-3-(2-formyl)ethylazetidine

1. N-Diphenylmethylazetidin-3-ol

Amlnocliphenylmethane (100 g, 0.54 mol) was added to a solution of epichlorohydrin (50 g, 0.54 mol) in DMSO (135 ml) and stirred at 25° C. for 3 days. The solution was then heated at 70° C. for 3 days before cooling to room temperature, adding 10% NaOH solution, and extracting with Et$_2$O (2×800 ml). The combined extracts were washed with water (2×11), dried (Na$_2$SO$_4$) and evaporated. The crude product was chromatographed on silica-gel eluting with CH$_2$Cl$_2$/MeOH (98:2) to give the title-azetidinol (33.5 g). δ (360 MHz, CDCl$_3$) 2.30 (1H, br s, OH), 2.87–2.91 (2H, m, 2 of CH of CH$_2$), 3.51–3.55 (2H, m, 2 of CH of CH$_2$), 4.34 (1H, s, CH), 4.41–4.48 (1H, m, CH—OH), 7.13–7.39 (10H, m, Ar—H).

2. N-Diphenylmethylazetidin-3-one

Triethylamine (112.1 g, 1.11 mol) was added to a solution of N-diphenylmethylazetidin-3-ol (26.6 g, 0.11 mol) in DMSO (300 ml). The solution was cooled to 10° C. and a solution of sulphur trioxide-pyridine complex (112 g, 0.7 mol) in DMSO (500 ml) added, rapidly. Stirring was continued at 10° C. for 0.75 h and the mixture then warmed to 25° C. and stirred for 1 h. The solution was poured into ice-water (21) and extracted with EtOAc (3×11). The combined extracts were washed with water (500 ml) and brine (500 ml) and dried ($Na_2SO_4$). The crude product was purified by chromatography through silica-gel eluting with petroleum ether/EtOAc (2:1) to give the desired ketone (25.8 g), mp 74°–75° C. δ (360 MHz, $CDCl_3$) 4.00 (4H, s, 2 of $CH_2$), 4.59 (1H, s, CH), 7.19–7.49 (10H, m, Ar—H).

3. Methyl (1-diphenylmethylazetidin-3-ylidene)acetate

Methyl diethylphosphonoacetate (11.0 g, 52.0 mmol) in THF (10 ml) was added dropwise to a stirred suspension of sodium hydride (2.1 g, 60% dispersion in oil, 52.5 mmol) in THF (40 ml), at 10° C. The mixture was stirred for 0.6 h and a solution of the preceding azetidinone (11.3 g, 48.0 mmol) in THF (50 ml) then added dropwise at 10° C. The mixture was heated at 50° C. for 3 h before removing the solvent under vacuum and redissolving the residue in $CH_2Cl_2$ (200 ml). The solution was washed with water (50 ml) and sodium bisulphite solution (2×50 ml) and dried ($Na_2SO_4$). Chromatography of the residue obtained, after removing the solvent, through silica-gel eluting with $CH_2Cl_2$/MeOH (98:2) gave the desired ester (13.1 g), mp 83°–84° C.; δ (360 MHz, $CDCl_3$) 3.65 (3H, s, $CO_2Me$), 3.88 (2H, m, 2 of CH of $CH_2$), 4.14–4.17 (2H, m, 2 of CH of $CH_2$), 4.52 (1H, s, CH), 5.65–5.68 (1H, m, vinyl-H), 7.17–7.44 (10H, m, Ar—H).

4. N-Diphenylmethyl-3-carbomethoxymethylazetidine

A mixture of the compound from step 3 (21.0 g, 71.7 mmol), $Pd(OH)_2$ (3.0 g, 20% on C), methanol (500 ml) and 2 N HCl (37 ml) was hydrogenated on a Parr shake apparatus for 2 h. The catalyst was removed by filtration through celite and the solvents removed under vacuum. Saturated $K_2CO_3$ solution was added (50 ml) and extracted with $CH_2Cl_2$ (2×250 ml). The combined extracts were washed with $H_2O$ (250 ml) and brine (100 ml), dried ($Na_2SO_4$) and evaporated to give the title-product as a pale yellow oil (19.3 g). δ (360 MHz, $CDCl_3$) 2.58 (2H, d, J=7.3 Hz, $CH_2$), 2.75–2.81 (3H, m, 2 of CH of $CH_2$ and CH), 3.35–3.38 (2H, m, 2 of CH of $CH_2$), 3.62 (3H, s, $CO_2Me$), 4.31 (1H, s, CH), 7.14–7.18, 7.23–7.27 and 7.38–7.40 (total 10H, each m, Ar—H).

5. Ethyl-2-(1-Diphenylmethylazetidin-3-yl)alcohol

Diisobutylaluminium hydride (119 ml of a 1M solution in toluene, 0.119 mol) was added dropwise to a stirred solution of the preceding ester (10.0 g, 33.9 mmol) in toluene (500 ml), at −35° C., over a 0.5 h period. The solution was warmed to 25° C., stirred for 2 h, and then cooled to 0° C. and quenched by addition of methanol (10 ml), 2N NaOH (5 ml) and $H_2O$ (5 ml). The mixture was warmed to 25° C., filtered through celite and the solvent removed under vacuum. The residue was chromatographed on silica-gel eluting with ethyl acetate/hexane (1:1) to give the title-alcohol as a white crystalline solid, (4.1 g), mp 98°–99° C. Found: C, 80.73; H, 8.06; N, 5.38. $C_{18}H_{21}NO$ requires C, 80.86; H, 7.92; N, 5.24%). δ (360 MHz, $CDCl_3$) 1.64 (1H, br s, OH), 1.82 (2H, m, $CH_2$), 2.51–2.58 (1H, m, CH), 2.87–2.91 and 3.29–3.33 (both 2H, each m, 2 of $CH_2$), 3.70 (2H, t, J=6.4 Hz, $CH_2$), 4.33 (1H, s, CH), 7.15–7.40 (10H, m, Ar—H).

6. Ethyl-2-(1-H-azetidin-3-yl)alcohol. Hydrochloride $Pd(OH)_2$ (0.8 g, 20% on C) was added to a solution of the preceding alcohol (4.0 g, 15.0 mmol) in methanol (200 ml) and 1N HCl (10 ml), and the mixture hydrogenated on a Parr shake apparatus for 24 h, at 55 psi. The mixture was filtered through celite and the solvent removed under vacuum. Diphenyl methane was removed by triturating the residue with ether and decanting. The remaining product was dried under vacuum to give the desired product (2.0 g); δ (250 MHz, $D_2O$) 1.86–1.94 (2H, m, $CH_2$), 2.98–3.16 (1H, m, CH), 3.60 (2H, t, J=6.4 Hz, $CH_2$), 3.86–3.96 and 4.14–4.22 (both 2H, both m, 2 of $CH_2$).

7. Ethyl-2-(1-tert-butyloxycarbonylazetidin-3-yl)alcohol

A mixture of the product from step 6 (1.44 g, 10.5 mmol), triethylamine (3.21 ml, 22.9 mmol) and $(BOC)_2O$ (3.43 g, 15.7 mmol), in THF (90 ml) was stirred at 25° C. for 2 days. The solvent was removed under vacuum, water (70 ml) added and extracted with EtOAc (3×). The combined extracts were dried ($MgSO_4$), evaporated and the residue chromatographed on silica-gel eluting with $CH_2Cl_2$/MeOH (95:5) to give the rifle-product (2.12 g). δ (250 MHz, $CDCl_3$) 1.42 (9H, s, 3 of $CH_3$), 1.56 (1H, s, OH), 1.82–1.90 (2H, m, $CH_2$), 2.56–2.76 (1H, m, CH), 3.58–3.67 (4H, m, $CH_2$ and 2 of CH of $CH_2$), 4.00–4.06 (2H, m, 2 of CH of $CH_2$).

8. Ethyl-2-(1-tert-butyloxycarbonylazetidin-3-yl)p-toluenesulphonate

A solution of p-toluenesulphonyl chloride (1.57 g, 8.2 mmol) in $CH_2Cl_2$ (20 ml) was added to a solution of the preceding alcohol (1.5 g, 7.46 mmol) and triethylamine (8.2 mmol) in $CH_2Cl_2$ (130 ml) at 0° C. A catalytic amount of DMAP was added and the mixture warmed to +25° C. and stirred for 16 h. The residue remaining afar removal of solvent under vacuum was chromatographed on silica-gel eluting with $CH_2Cl_2$MeOH (99:1) to give the desired tosylato (1.7 g, 71%). δ (360 MHz, $CDCl_3$) 1.42 (9 H, s, 3 of $CH_3$), 1.91–1.97 (2H, m, $CH_2$), 2.46 (3H, s, $CH_3$), 2.53–2.61 (1H, m, CH), 3.51 (2H, dd, J=5.5 and 8.6 Hz, 2 of CH of $CH_2$), 3.95 (2H, dd, J=8.5 and 8.6 Hz, 2 of CH of $CH_2$), 4.01 (2H, t, J=6.1 Hz, $CH_2$—OTs), 7.36 (2H, d, J=8.1 Hz, Ar—H), 7.78 (2H, d, J=8.1 Hz, Ar—H).

9. Ethyl-2-(1-tert-butyloxycarbonylazetidin-3-yl)nitrile

NaCN (0.35 g, 7.1 mmol) was added to a solution of the preceding tosylate (1.7 g) in anhydrous DMSO (40 ml) and the mixture stirred at 60° C. for 16 h. Saturated $NH_4Cl$ solution (30 ml) was added and the mixture extracted with $CH_2Cl_2$ (300 ml). The $CH_2Cl_2$ extract was washed with $H_2O$ (4×), dried ($NaSO_4$) and evaporated. The crude product was purified by chromatography on silica-gel eluting with $CH_2Cl_2$/MeOH (98:2). The product was Obtained as a clear oil (0.92 g, 92%); δ (3601 MHz, $CDCl_3$) 1.44 (9H, s, 3 of $CH_3$), 1.94–2.00 (2H, m, $CH_2$), 2.34 (2H, t, J=7.1 Hz, $CH_2CN$), 2.61–2.69 (1H, m, CH), 3.59 (2H, dd, J=5.4 and 8.7 Hz, 2 of CH of $CH_2$), 4.07 (2H, dd, J=8.4 and 8.7 Hz, 2 of CH of $CH_2$).

10. N-tert-Butyloxycarbonyl-3-(2-formyl)ethylazetidine

Diisobutylaluminium hydride (6.43 ml of a 1M solution in toluene, 6.4 mmol) was added to a solution of the preceding nitrile (0.9 g, 4.3 mmol) in toluene (100 ml), at −60° C. The solution was warmed to +25° C. and stirred for 5 h before adding saturated $NH_4Cl$ solution (50 ml) and stirring for 16 h. The mixture was extracted with $CH_2Cl_2$ (3 x), the combined extracts dried ($Na_2SO_4$) and the residue remaining, after removal of solvents under reduced pressure, chromatographed on silica gel, eluting with CH$_2$Cl$_2$/MeOH (98:2) to give the title-aldehyde (0.42 g, 46%); δ (250 MHz, CDCl$_3$) 1.44 (9H, s, 3 of CH$_3$), 1.86–1.96 (2H, m, CH$_2$), 2.40–2.60 (3 H, m, CH and CH$_2$), 3.53 (2H, dd, J=5.4 and 8.7 Hz, 2 of CH of CH$_2$), 4.00 (2H, dd, J=8.5 and 8.6 Hz, 2 of CH of CH$_2$).

N-H-3-[5-(1,2,4-Triazol-1-ylmethyl), 1H-indol-3-yl]methylazetidine

A mixture of the preceding aldehyde (0.4 g, 1.88 mmol) and 1-(4-hydrazinophenyl)methyl-1,2,4-triazole hydrochloride (0.51 g, 2.26 mmol) in 4% H$_2$SO$_4$ was heated at reflux for 3 h. The solution was cooled to 0° C., basified (K$_2$CO$_3$) and extracted with EtOAc (3×). The combined extracts were dried (MgSO$_4$), evaporated, and the residue purified by chromatography on silica-gel eluting with CH$_2$Cl$_2$/MeOH/NH$_3$ (15:8:1). The product (0.16 g, 34%) was obtained as a colourless foam; δ (360 MHz, D$_4$—MeOH) 2.94 (2H, d, J=7.6 Hz, CH$_2$), 3.04–3.16 (1H, m, CH), 3.46–3.54 and 3.68–3.74 (both 2H, each m, 2 of CH$_2$), 5.36. (2H, s, CH$_2$), 7.02 (1H, s, Ar—H), 7.03 (1H, dd, J=1.5 and 8.4 Hz, Ar—H), 7.25 (1H, d, J=8.4 Hz, Ar—H), 7.48 (1H, s, Ar—H), 7.87 (1H, s, Ar—H), 8.35 (1H, s, Ar—H).

N-Methyl-3-[5-(1,2,4-triazol-1-ylmethyl)-1H-indol-3-yl] methylazetidine. 0.65 Oxalate To a cooled solution of the preceding 1H-azetidine (0.16 g, 0.60 mmol), NaCNBH$_3$ (45 mg, 0.72 mmol) and acetic acid (90.0 mg, 1.5 mmol), in methanol (12 ml), was added a solution of formaldehyde (57.0 mg, 0.72 mmol; 38% w/v) in methanol (13 ml), at such a rate as to keep the temperature of the solution at 0° C. The mixture was stirred at 0° C. for 0.25 h and then warmed to room temperature and stirred for 1 h. Saturated K$_2$CO$_3$ solution (15 ml) was added and the solvent removed under vacuum. The aqueous was extracted with EtOAc (4×), the combined extracts dried (MgSO$_4$) and the solvent evaporated. The crude product was chromatographed on silica-gel eluting with CH$_2$Cl$_2$EtOH/NH$_3$ (70:8:1) to give the title-product (0.12 g, 71%). The 0.65 oxalate salt was prepared, mp 209°–210° C. Found: C, 61.31; H, 6.21; N, 20.23. CC$_{16}$H$_{19}$N$_5$.0.65 (C$_2$H$_2$O$_4$) requires C, 61.14; H, 6.02; N, 20.61%); δ (360 MHz, D$_2$O) 2.75 and 2.91 (total 3H, each s, N—CH$_3$), 3.04 and 3.09 (total 2H, each d, J=7.7 Hz, CH$_2$), 3.26–3.37 (1H, m, CH), 3.77 and 3.98 (total 2H, each dd, J=9.0 and 11.0 Hz, 2 of CH of CH$_2$), 4.14 and 4.32 (total 2H, each dd, J=6.3 and 11.0 Hz, 2 of CH of CH$_2$), 5.12 (2H, s, CH$_2$), 7.21 (1H, d, J=8.4 Hz, Ar—H), 7.28 (1H, s, Ar—H), 7.51 (1H, dd, J=1.5 and 8.4 Hz, Ar—H), 7.60 and 7.63 (total 1H, each s, Ar—H), 8.05 (1H, s, Ar—H), 8.54 (1H, s, Ar—H).

EXAMPLE 4

(±)N-Methyl-2-[5-(1,2,4-triazol-1-ylmethyl)-1H-indol-3-yl]methylpyrrolidine. Hydrogen Oxalate. 0.2 Hydrate

INTERMEDIATE 5

(±)-N-tert,Butyloxycarbonyl-2-(2-formyl)ethyl pyrrolidine

1. N-tert-Butyloxycarbonylpyrrole-2-carboxaldehyde

A mixture of pyrrole-2-carboxaldehyde (9.5 g, 0.1 mol), (BOC)$_2$O (24.0 g, 0.11 mol) and DMAP (0.25 g) in THF (150 ml) was stirred at room temperature for 16 h. The solvent was removed under vacuum and the residue dissolved in CH$_2$Cl$_2$ (200 ml) and washed with 10% citric add, water and brine. The organic layer was dried (Na$_2$SO$_4$) and evaporated to give the desired product (20.9 g, 95%); δ (360 MHz, CDCl$_3$) 1.65 (9H, s, 3 of CH$_3$), 6.28–6.30 (1H, m, Ar—H), 7.18–7.19 (1H, m, Ar—H), 7.43–7.45 (1H, m, Ar—H). 2. trans-Methyl-2-N-tert-butyloxycarbonylpyrrol-2-yl)acrylate Prepared from the preceding aldehyde and methyl diethylphosphonoacetate as described for Intermediate 4 (step 3). The product (98%) was obtained as a pale yellow oil; δ (360 MHz, CDCl$_3$) 1.63 (9H, s, 3 of CH$_3$), 3.78 (3H, s, CH$_3$), 6.21 (1H, d, J=16.0 Hz, vinyl CH), 6.21–6.22 (1H, m, Ar—H), 6.69–6.71 (1H, m, Ar—H), 7.38–7.39 (1H, m, Ar—H), 8.30 (1H, d, J=16.0 Hz, vinyl CH).

3. (±)-Methyl-2-(N-tert-butyloxycarbonylpyrrolidin-2-yl) propionate

A solution of the product from step 2 (11.0 g, 43.8 mmol) in glacial AcOH (300 ml) was hydrogenated over PtO$_2$ (1.25 g) at 50 psi. The catalyst was removed by filtration through hyflo and the solvent removed under vacuum. The crude product was chromategraphed on silica-gel eluting with diethyl ether:petroleum ether (1:1) to give the title-ester (7.4 g, 67%); δ (360 MHz, CDCl$_3$) 1.46 (9H, s, 3 of CH$_3$), 1.53–2.07 (6H, m, 3 of CH$_2$), 2.24–2.40 (2H, m, CH$_2$), 3.25–3.46 (2H, m, CH$_2$), 3.67 (3H, s, CO$_2$CH$_3$), 3.61–3.66 (1H, m, CH).

4. (±)-N-tert-Butyloxycarbonyl-2-(2-formyl) ethylpyrrolidine

To a cooled (−78° C.) solution of the preceding ester (4.0 g, 15.56 mmol) in anhydrous toluene (75 ml) was added dropwise a solution of diisobutylaluminium hydride (18.7 ml of a 1M solution in toluene, 18.7 mmol), at such a rate as to maintain the temperature below −75° C. After the addition was complete the reaction was stirred at −78° C. for 4 h before adding MeOH (1 ml), H$_2$O (1 ml) and sodium hydroxide (2N, 1 ml), successively, dropwise. The mixture was warmed to room temperature and the precipitated salts removed by filtration through hyflo. The filtrate was dried (MgSO$_4$) and the solvent removed under vacuum. The residue was chromatographed on silica-gel eluting with ethyl acetate/petroleum ether (3:4) to give the title-compound (2.74 g, 78%) as a colourless oil; δ (360 MHz, CDCl$_3$) 1.46 (9H, s, 3 of CH$_3$), 1.58–1.99 (6H, m, 3 of CH$_2$), 2.45 (2H, d t, J=1.2 and 7.5 Hz, CH$_2$—CHO), 3.25–3.39 (2H, m, CH$_2$), 3.78–3.88 (1H, m, CH), 9.76 (1H, t, J=1.2 Hz, CHO).

(±)-N-Methyl-2-[5-(1,2,4-triazol-1-ylmethyl)-1H-indol-3-yl]methylpyrrolidine. Hydrogen Oxalate. 0.2 Hydrate.

Prepared from (±)N-tert-butyloxycarbonyl-2-(2-formyl) ethylpyrrolidine and 1-(4-hydrazinophenyl)methyl-1,2,4-triazole hydrochloride as described for Example 3. The hydrogen oxalate salt was prepared, mp 161°–162° C. (MeOH/ether). Found: C, 57.97; H, 5.82; N, 17.53. C$_{17}$H$_{21}$N$_5$.C$_2$H$_2$O$_4$.0.2 H$_2$O requires C, 57.94; H, 5.98; N, 17.53%); δ (360 MHz, D$_2$O) 1.81–2.25 (4H, m, CH$_2$), 2.84 (3H, s, CH$_3$), 3.08–3.18, 3.29–3.35 and 3.65–3.74 (2H, 1H, and 2H respectively, each m, 2 of CH$_2$ and CH), 5.52 (2H, s, CH$_2$), 7.22 (1H, d, J=8.4 Hz, Ar—H), 7.36 (1H, s, Ar—H), 7.53 (1H, d, J=8.4 Hz, Ar—H), 7.63 (1H, s, Ar—H), 8.08 (1H, s, Ar—H), 8.59 (1H, s, Ar—H).

EXAMPLE 5

(2R ) N-Methyl-2-[5-(1,2,4-triazol-4-yl)-1H-indol-3-yl] methylpyrrolidine. 1.3 Benzoate. 0.9 Hydrate

INTERMEDIATE 6

4'-(1,2,4-Triazol-4-yl)phenylhydrazine 1. 4'-Aminoacetanilide

A solution of 4-nitroacetanilide (5.0 g, 27.8 mmol) in EtOH/EtOAc (160 ml, 1:1), $H_2O$ (15 ml) and 5N HCl (5.6 ml, 28.0 mmol) was hydrogenated over 10% Pd-C (0.50 g) at 50 psi for 0.25 h. The catalyst was removed by filtration through celite and the solvents removed under vacuum. The free base was generated by dissolving the product in $H_2O$, basifying with 2N NaOH and extracting into EtOAc. The combined extracts were dried ($MgSO_4$) and evaporated to give the title-aniline (3.75 g, 90%). δ (250 MHz, $CDCl_3$/ $d_4$—MeOH) 2.10 (3H, s, $CH_3$), 6.68 (2H, d, J=8.8 Hz, Ar—H), 7.27 (2H, d, J=8.8 Hz, Ar—H).

2. 4'-(1,2,4-Triazol-4-yl)acetanilide

A mixture of the preceding aniline (3.52 g, 23.4 mmol), N,N-dimethylformamide azine (3.33 g, 23.4 mmol; *J. Chem. Soc.*, (C) 1967, 1664) and p-toluenesulphonic acid monohydrate 25. (0.223 g, 1.17 mmol), in anhydrous toluene (100 ml), was heated at reflux for 17 h. The beige coloured precipitate was filtered off and washed with toluene and $CH_2Cl_2$ and dried under vacuum to give the desired triazole (4.29 g, 91%); a (250 MHz, $d_4$—MeOH/$d_6$—DMSO) 2.14 (3H, s, $CH_3$), 7.60 (2H, d, J=8.8 Hz, Ar—H), 7.78 (2H, d, J=8.8 Hz, Ar—H), 8.96 (2 H, s, Ar—H).

3. 4'-(1,2,4-Triazol-4-yl)phenylaniline

A solution of the preceding acetanilide (4.91 g, 24.3 mmol) in 5N HCl (100 ml) was heated at 125° C. for 1.5 h. The mixture was cooled to 0° C., basified with concentrated aqueous NaOH solution and extracted with $CH_2Cl_2$ (×5). The combined extracts were dried ($MgSO_4$) and evaporated and the residue chromatographed on silica gel, eluting with $CH_2Cl_2$/MeOH/$NH_3$ (80:8:1), to give the title-aniline (2.94 g, 76%); δ (250 MHz, $CDCl_3$) 3.80 (2H, s, $NH_2$), 6.71 (2H, d, J=8.8 Hz, Ar—H), 7.08 (2H, d, J=8.8 Hz, Ar—H), 8.36 (2H, s, Ar—H).

4. 4'-(1,2,4-Triazol-4-yl)phenylhydrazine

To a solution of the preceding aniline (1.60 g, 9.99 mmol) in concentrated HCl/$H_2O$ (23 ml and 3 ml respectively) was added, at −21° C., a solution of $NaNO_2$ (0.69 g, 9.99 mmol) in $H_2O$ (8 ml), at such a rate as to maintain the temperature below −10° C. The mixture was stirred for 0.3 h and then filtered rapidly through a sinter, under vacuum. The filtrate was added to a cooled (−20° C.) solution of $SnCl_2.2H_2O$ (9.02 g, 40.0 mmol) in concentrated HCl (17 ml). The mixture was stirred at −20° C. for 0.25 h and at room temperature for 1.25 h. The resulting solid was filtered off, washed with $Et_2O$ and dried under vacuum. The crude product was dissolved in $H_2O$, basified with concentrated aqueous NaOH and extracted with EtOAc (×5). The combined extracts were dried ($MgSO_4$) and evaporated to afford the rifle-product (0.95 g, 54%); δ (250 MHz, $CDCl_3$/$d_4$— MeOH) 3.98 (3H, br s, NH and $NH_2$); 6.97 (2H, d, J=12.0 Hz, Ar—H); 7.25 (2H, d, J=12.0 Hz, Ar—H); 8.48 (2H, s, Ar—H).

INTERMEDIATE 7

(2R)-N-tert-Butyloxycarbonyl-3-(pyrrolidin-2-yl)propanal 1. (2R)-N-tert-Butyloxycarbonylpyrrolidin-2-ylmethanol A solution of di-tert-butyl dicarbonate (34.11 g, 156.3 mmol) in DCM (125 ml) was added dropwise to a stirred solution of D-prolinol (15.04 g, 148.7 mmol) in $CH_2Cl_2$ (125 ml) at 0° C. under nitrogen. The mixture was stirred at 0° C. for 1 h and then at room temperature for 66 h. Evaporation of the solvent afforded the title-carbamate (29.9 g, 100%); δ (360 MHz, $CDCl_3$) 1.47 (9H, s, $^t$Bu), 1.60 (1H, br m, $CH_2$), 1.72–1.89 (2H, m, $OH_2$), 2.00 (1H, m, $CH_2$), 3.31 (1H, m, $CH_2$), 3.46 (1H, m, $OH_2$), 3.55–3.66 (2H, m, $CH_2$), 3.95 (1H, br m, $CH_2$).

2. (2R)-N-tert-Butyloxycarbonylpyrrolidin-2-ylmethanol

DMSO (8.63 ml, 122 mmol) was added dropwise to a stirred solution of oxalyl chloride (5.31 ml, 60.9 mmol) in $CH_2Cl_2$ (350 ml) at −78° C. under nitrogen. The mixture was stirred at this temperature for 30 mins before adding a solution of the preceding alcohol (10.20 g, 50.68 mmol) in $CH_2Cl_2$ (120 ml). After stirring at −78° C. for 95 mins, triethylamine (35.5 ml, 255 mmol) was added dropwise and the mixture allowed to warm to room temperature. Water was added, the mixture extracted with $CH_2Cl_2$ and the combined extracts dried ($MgSO_4$) and evaporated. The residue was purified by flash chromatography on silica gel, eluting with 1:1 ethyl acetate/hexane, to afford the titlealdehyde (10.1 g, 100%); δ (360 MHz, $CDCl_3$) 1.38 and 1.41 (9H, 2×s, $^t$Bu), 1.79–2.06 (4H, m, $CH_2$), 3.39–3.48 (2H, m, $CH_2$), 3.98 and 4.14 (1H, 2×m, $CH_2$), 9.40 and 9.49 (1H, 2×s, CHO).

3. (2R)-trans-Methyl[N-tert-butyloxycarbonyl-3-(pyrrolidin- 2-yl)]propenoate

Methyl diethylphosphonoacetate (3.71, 20.2 mmol) was added dropwise to a stirred suspension of sodium hydride (0.81 g, 60% dispersion in oil, 20.3 mmol) in THF (30 ml) at 4° C. under nitrogen. The mixture was stirred at room temperature for 0.5 h, recooled to 2° C. and a solution of the preceding aldehyde (4.03 g, 20.2 mmol) in THF (35 ml) added dropwise, maintaining the temperature below 10° C. The mixture was stirred at 7.5° C. for 2.5 h before evaporating the solvent in vacuo and redissolving the residue in $CH_2Cl_2$. The solution was washed with water (×1), 20% w/v sodium bisulphite solution (×2) and water (×1), dried ($MgSO_4$) and evaporated. Flash chromatography on silica gel of the residue, eluting with 40:60 ethyl acetate/hexane, afforded the title—ester (4.92 g, 95%); δ (360 MHz, $CDCl_3$) 1.42 (9H, br s, $^t$Bu), 1.78–1.88 (3H, m, $CH_2$), 2.08 (1H, m, $CH_2$), 3.44 (2H, br s, $CH_2$), 3.74(3H, s, $CO_2Me$), 4.37–4.50 (1H, m, CH), 5.83 (1H, d, J=15.2 Hz, vinyl CH), 6.83 (1H, m, vinyl CH).

4. (2R)-Methyl [N-tert-butyloxycarbonyl-3-(pyrrolidine2-yl) propanoate

A mixture of the preceding olefinic ester (4.34 g, 17.0 mmol) 10% Pd/C (0.43 g), methanol (30 ml) and water (10 ml) was hydrogenated on a Parr shake apparatus for 2 h. The catalyst was removed by filtration through celite and the solvents evaporated in vacuo. Flash chromatography of the residue on silica gel, eluting with 30:70 ethyl acetate/ hexane, afforded the title—ester (4.21 g, 96%); $[α]_D$+36.5° (c 0.37, $CH_2Cl_2$); δ (360 MHz, $CDCl_3$) 1.46 (9H, s, $^t$Bu), 1.54–2.02 (6H, m, $CH_2$), 2.33 (2H, t, J=7.8 Hz, m, $CH_2$), 3.29 (1H, m, $CH_2$), 3.39 (1H, m, $CH_2$), 3.67 (3H, s, $CO_2Me$), 3.81 (1H, m, CH).

5. (2R)-N-tert-Butyloxycarbonyl-3-(pyrrolidin-2-yl)propanal

Prepared from the preceding ester using the procedure described for the preparation of Intermediate 5 (step 4). δ (250 MHz, $CDCl_3$) 1.46 (9H, s, $^t$Bu), 1.58–1.99 (6H, m, $CH_2$), 2.45 (2H, dt, J=1.2 and 7.5 Hz, $CH_2$—CHO), 3.25–3.39 (2H, m, CH$_2$), 3.83 (1H, m, CH), 9.76 (1H, t, J=1.2 Hz, CHO).

(2R)-2-[5-(1,2,4-Triazol-4-yl)-1H-indol-3-yl]methylpyrrolidine

A solution of 4'-(1,2,4-triazol-4-yl)phenylhydrazine dihydrochloride (1.12 g, 4.49 mmol) and (2R)-N-tert-butyloxycarbonyl- 3-(pyrrolidin-2-yl)propanal (0.847 g, 3.73 mmol) in 4% aqueous sulphuric acid (80 ml) was stirred at room temperature for 0.5 h and then heated at reflux for 25 h. After cooling to room temperature, n-butanol was added and the aqueous basified with saturated aqueous potassium carbonate solution. The aqueous was separated and extracted further with n-butanol (×2). The combined organics were evaporated in vacuo and the residue flash chromategraphed on silica gel eluting with CH$_2$CCl$_2$/MeOH/NH$_3$ (20:8:1), to give the title—pyrrolidine (0.263 g, 26%); δ (360 MHz, d$^4$—MeOH) 1.47 (1H, m, CH$_2$), 1.68–1.94 (3H, m, CH$_2$), 2.61 (1H, m, CH$_2$), 2.92 (1H, d, J=6.8 Hz, CH$_2$), 3.01 (1H, m, CH$_2$), 3.42 (1H, pentet, J=7.4 Hz, CH), 7.19–7.22 (2H, m, Ar—H), 7.43 (1H, d, J=8.7 Hz, Ar—H), 7.71 (1H, d, J=1.8Hz, Ar—H), 8.82 (2H, s, Ar—H).

(2R)-N-Methyl-2-[5-(1,2,4-triazol-4-yl)-1H-indol-3-yl]methylpyrrolidine. 1.3 Benzoate. 0.9 Hydrate.

Prepared from the preceding pyrrolidine using the procedure described for Example 3. The benzoate salt was prepared; (Found: C, 66.13; H, 6.34; N, 15.19. C$_{16}$H$_{19}$N$_5$.1.3(C$_7$H$_6$O$_2$). 0.9(H$_2$O) requires C, 66.06; H, 6.32; N, 15.35%); δ (360 MHz, D$_2$O) 1.86–2.09 (3H, m, CH$_2$), 2.27 (1H, m, CH$_2$), 2.86 (3H, s, CH$_3$), 3.13–3.21 (1H, m, CH$_2$), 3.38 (1H, dd, J=14.8 and 6.0 Hz, CH$_2$), 3.68–3.76 (2H, m, CH$_2$), 7.34 (1H, dd, J=8.6 and 2.0 Hz, Ar—H), 7.46–7.60 (5H, m, Ar—H), 7.65 (1H, d, J=9.0 Hz, Ar—H), 7.76 (1H, d, J=2.0 Hz, Ar—H), 7.88–7.91 (2.5H, m, Ar—H), 8.82 (2H, s, Ar—H).

EXAMPLE 6

3-[trans-1-(Dimethylamino)cyclobutan-3-yl]-5-[(1,2,4-triazol- 1-yl) methyl]-1H-indole and 3-[cis-1-(Dimethylamino)cyclobutan- 3-yl]-5-[(1,2,4- triazol-1-yl)methyl]-1H-indole. Hydrogen Oxalates.

1. cis/trans-1-Benzyloxy-3-(tert,butyloxycarbonyl amino)cyclobutane

To a stirred solution of cis/trans-3-benzyloxycyclobutane 1-carboxylic add (5.0 g, 24.24 mmol) (*Coll. Czech. Chem. Commun.*, 1981, 47, 2440) in anhydrous 2-methyl-2-propanol (70 ml) was added anhydrous triethylamine (3.72 ml, 26.67 mmol) followed by diphenylphosphoryl azide (5.48 ml, 25.45 mmol) and the resulting colourless clear solution was refluxed for 19 hours under a nitrogen atmosphere. Solvents were removed under vacuum and the remaining liquid was dissolved in ethyl acetate (200 ml) and it was washed with 1N hydrochloric add (1×50 ml), water (1×50 ml), 10% aqueous sodium bicarbonate (1×50 ml), brine (1×20 ml), then dried (MgSO$_4$) and concentrated. Flash chromatography of the residue (silica gel, hexane-ethyl acetate, 85:15 to 70:30) gave 3.30 g of the title compound (cis/trans 1:1) as a white solid; δ (250 MHz, CDCl$_3$) 7.38–7.25 (5H, m, Ph—), 4.63 (1H, br s, —NH—), 4.40 (2H, s, PhCH$_2$—), 4.26–4.12 (1H, m, —CH—O), 3.75 (1H, qn, J=7.5 Hz, —CH—N), 2.78–2.64 (1H, m, —CH$_2$—), 2.50–2.36 (1H, m, —CH$_2$—), 2.20–2.06 (1H, m, —CH$_2$—), 1.88–1.74 (1H, m, —CH$_2$—), 1.44 (9H, s, t—Bu); m/z (CI) 276 (M$^-$–1).

2. cis/trans-3-(tert-Butyloxycarbonyl amino)cyclobutan-1-ol

A solution of cis/trans-1-benzyloxy-3-(tertbutyloxycarbonylamino) cyclobutane (3.0 g) in absolute ethanol (40 ml) was hydrogenated at 20 psi over 10% palladium on carbon (540 mg) for 2 hours. The catalyst was removed by filtration, washed with ethanol (2×20 ml) and the filtrate was concentrated under vacuum to give 2.05 g (100%) of the title compound (cis/trans, 1:1) as a waxy white solid; mp 64°–67° C. (hexane-ethyl acetate); δ (250 MHz, CDCl$_3$) 4.64 (2H, br s, —NH—), 4.54–4.42 (1H, m, —CH—), 4.28–4.14 (1H, m, —CH—), 4.02 (1H, qn, J=7.3Hz, —CH—), 3.74–3.56 (1H, m, —CH—), 2.84–2.70 (2H, m, —CH$_2$—), 2.40–2.14 (4H, m, —CH$_2$), 1.88–1.70 (4H, m, —CH$_2$— and —OH), 1.43 (18H, s, t—Bu); m/z (CI) 187 (M$^-$). (Found: C, 58.02; H, 9.02; N, 7.25. C$_9$H$_{17}$NO$_3$ requires: C, 57.73; H, 9.15; N, 7.48%.)

3. 3-(tert-Butyloxycarbonylamino)cyclobutan-1-one

To a stirred solution of the product from the previous step (500 mg, 2.67 mmol) and N-methylmorpholine N-oxide monohydrate (541 mg, 4.0 mmol) in anhydrous dichloromethane (27 ml) were added 4 Å molecular sieves (500 mg) and the mixture was stirred for 15 minutes prior to the addition of tetrapropylammonium perruthenate (47 mg, 0.13 mmol). After being stirred for 1.5 hours under a nitrogen atmosphere, the mixture was diluted with dichloromethane (100 ml) and it was washed with 10% aqueous sodium sulphite (1×25 ml), brine (1×25 ml) and saturated aqueous copper (II) sulphate (1×25 ml). The organic solution was filtered through a plug of flash silica gel (40 g) and this was washed with ethyl acetate (3×20 ml). The filtrate was concentrated under vacuum and the remaining residue was purified by flash chromatography (silica gel, hexane-ethyl acetate, 60:40) to give 410 mg (83%) of the title compound as a white solid; mp 75°–78° C.; δ (360 MHz, CDCl$_3$) 4.90 (1H, br s, —NH—), 4.32–4.22 (1H, m, —CH—), 3.46–3.34 (2H, m, —CH$_2$—), 3.08–2.98 (2H, m, —CH$_2$—), 1.46 (9H, s, t—Bu); m/z (CI) 186 (M$^+$+1). (Found: C, 58.31; H, 7.96; N, 7.59. C$_9$H$_{15}$NO$_3$ requires: C, 58.36; H, 8.16; N, 7.56%.)

4. 1-(tert-Butyloxycarbonylamino)- 3-(carbomethoxymethylene)cyclobutane

To a cooled (−70° C.) and stirred solution of trimethyl phosphonoacetate (1.5 g) in anhydrous tetrahydrofuran (40 ml) was added potassium bis(trimethylsilyl)amide (0.5M in toluene; 15.07 ml) at such a rate as to maintain the internal temperature below −62° C. (ca 8 min). After 15 minutes of stirring at −70° C., a solution of 3-(tert-butyloxycarbonylamino)cyclobutan-1-one (1.27 g) in anhydrous tetrahydrofuran (10 ml) was added over 9 minutes, under a nitrogen atmosphere. The mixture was then allowed to warm to room temperature and it was stirred for 1 hour before it was quenched with saturated aqueous ammonium chloride (40 ml). Products were extracted with ethyl acetate (2×50 ml) and the combined organic solutions were washed with brine (1×40 ml), dried (MgSO$_4$) and concentrated. Flash chromatography of the residue (silica gel, hexane-ethyl acetate, 75:25) gave 1.61 g (97%) the title compound as a white solid; mp 79°–82° C. δ (250 MHz, CDCl$_3$) 5.70 (1H, m, —CH—), 4.81 (1H, br s, —NH—), 4.32–4.13 (1H, m, —CH—), 3.69 (3H, s, —OMe), 3.64–3.50 (1H, m, —CH$_2$—), 3.26–3.10 (1H, m, —CH$_2$—), 3.00–2.86 (1H, m, —CH$_2$—), 2.80–2.68 (1H, m, —CH$_2$—), 1.45 (9H, s, t—Bu); m/z (CI) 240 (M$^-$–1). (Found: C, 60.28; H, 7.87; N, 5.76. C$_{12}$H$_{19}$NO$_4$×0.03 C$_6$H$_{14}$ requires: C, 59.99; H, 8.02; N, 5.75%.)

5. cis/trans-1-(tert-Butyloxycarbonylamino)- 3-(carbomethoxymethyl)cyclobutane

A solution of the product from the previous step (1.5 g) in absolute ethanol (40 ml) was hydrogenated at atmospheric pressure over 10% palladium on carbon (200 mg) for 2 hours. The catalyst was filtered off, washed with ethanol (1×25 ml) and the solvent was removed under vacuum to give the title compound (1.48 g, 98%) as a white solid (cis/trans ca 2:1); mp 69°–73° C.; m/z (CI) 243 (M⁻).

6. [cis/trans-1-(tert-Butyloxycarbonylamino)cyclobutan-3-yl]acetaldehyde

To a cooled (−79° C.) and stirred solution of the product from the previous step (1.46 g, 6.0 mmol) in anhydrous toluene (90 ml) was added dropwise via cannula diisobutylaluminium hydride (1M in toluene; 15 ml) at such a rate as to maintain the internal temperature below −78° C. (ca 18 minutes). The resulting mixture was stirred at −80° C. for 1 hour before anhydrous methanol (4.9 ml) was added dropwise at such a rate as to maintain the temperature below −78° C. Aqueous citric acid (10%; 75 ml) was added and the mixture was allowed to warm to room temperature. Products were extracted with ethyl acetate (3×100 ml), washed with brine (1×70 ml), dried (MgSO₄) and concentrated. Flash chromatography of the residue (silica gel, hexane-ethyl acetate, 60:40) gave 1.22 g (95%)of the title aldehyde as a thick colourless oil which solidified on standing; δ (250 MHz, CDCl₃) 11.25 (1H, s, —CHO); m/z (CI) 212 (M⁻−1).

7. 3-[trans-1-(Dimethylamino)cyclobutan-3-yl]-5-[(1,2,4-triazol-1-yl)methyl]-1H-indole and 3-[cis-1-(Dimethylamino) cyclobutan-3-yl]-5-[(1,2,4triazol-1-yl)methyl]-1H-indole. Hydrogen oxalates.

To a solution of the aldehyde from the previous step (1.06 g, 4.97 mmol) in absolute ethanol (2.5 ml) was added 4% aqueous sulfuric acid (5 ml) followed by 1-(4-hydrazinophenyl) methyl-1,2,4-triazole dihydrochloride (1.3 g, 4.97 mmol). After being stirred for 1 minute, 4% aqueous sulfuric acid (40 ml) was slowly added over 5 minutes and the reaction mixture was refluxed for 1 hour and 20 minutes. After being cooled to room temperature, methanol (100 ml) was added and the mixture was basified with saturated aqueous potassium carbonate (20 ml). The precipitated solids were filtered off, washed with methanol (2×30 ml) and solvents were removed under vacuum. The remaining residue was triturated with hot ethanol (50 ml) and the undissolved solid was removed by filtration and washed with ethanol (2×30ml). The resulting clear filtrate was concentrated under vacuum and the residue was purified by flash chromatography (silica gel, dichloromethane-methanol-ammonia, 85:15:1.5) to give 545 mg (41%) of 3-(1-aminocyclobutan-3-yl)- 5-[(1,2,4-triazol-1-yl)methyl]-1H-indole as a mixture of cis and trans isomers.

To a cooled (0° C.) and stirred solution of cis/trans-3-(1-aminocyclobutan-3-yl)-5-[(1,2,4-triazol-1-yl)methyl]-1H-indole (270 mg, 1.0 mmol) in anhydrous methanol (20 ml) were added sodium cyanoborohydride (127 mg, 2.0 mmol), glacial acetic acid (289 μl, 5.0 mmol) and a solution of formaldehyde (38% w/v aqueous solution; 200 μl) in absolute methanol (3 ml). The reaction mixture was then allowed to warm to room temperature and it was stirred for 1.5 hours before saturated aqueous potassium carbonate (10 ml) was added and the methanol was removed under vacuum. The aqueous residue was extracted with ethyl acetate (3×50 ml) and the combined organic solutions were washed with brine (2×15 ml), dried (Na₂SO₄) and concentrated. The remaining residue was purified by preparative TLC (silica gel, dichloromethane-methanol-ammonia, 90:10:1) to give 102 mg (34%) of 3-[cis-1-(dimethylamino)cyclobutan-3-yl]-5-[( 1,2,4-triazol-1-yl)methyl]-1H-indole (less polar isomer) and 132 mg (44%) of 3-[trans-1-(dimethyl amino)cyclobutan-3-yl]-5-[(1,2,4-triazol-1-yl)methyl]-1H-indole (more polar isomer). The hydrogen oxalate salts were prepared and showed:

Cis-ISOMER: mp 223°–226° C. (ethanol-methanol); δ (250 MHz, D₂O) 8.54 (1H, s, Ar—H), 8.05 (1H, s, Ar—H), 7.63 (1H, br d, Ar—H), 7.50 (1H, d, J=8.4 Hz, Ar—H), 7.28 (1H, s, Ar—H), 7.20 (1H, dd, J=8.4 and 1.8 Hz, Ar—H), 5.50 (2H, s, Ar—CH₂), 3.82–3.68 (1H, m, —CH—), 3.54–3.36 (1H, m, —CH—), 2.96–2.80 (8H, m and s, —CH₂— and —NMe₂), 2.36–2.20 (2H, m, —CH₂—). (Found: C, 59.20; H, 6.37; N, 17.78. C₁₇H₂₁ N₅×1.0 C₂H₂O₄ requires: C, 59.21; H, 6.02; N, 18.17%.)

Trans-ISOMER: mp 137°–139° C. (ethanol); δ (250 MHz, D₂O) 8.54 (1H, s, Ar—H), 8.05 (1H, s, Ar—H), 7.54 (1H, br s, Ar—H), 7.51 (1H, d, J=8.5 Hz, Ar—H), 7.35 (1H, s, Ar—H), 7.22 (1H, dd, J=8.5 and 1.8 Hz, Ar—H), 5.49 (2H, s, Ar—CH₂—), 3.94–3.66 (2H, m, —CH—), 2.84–2.66 (8H, s and m, —NMe₂ and —CH₂—), 2.62–2.48 (2H, m, —CH₂—); m/z (CI) 296 (M⁺+1). (Found: C, 59.33; H, 6.28; N, 17.82. C₁₇H₂₁ N₅×1.0 C₂H₂O₄ requires: C, 59.21; H, 6.02; N, 18.17%.)

An X-ray crystal structure was obtained for the cis-ISOMER hydrogen oxalate which confirmed the initial assignment based on experiments carded out on the free bases.

EXAMPLE 7

N-2-[5-(1,2,4-Triazol-4-yl)-1H-indol-3-yl]ethylazetidine. Oxalate. 1.6 Hydrate

A mixture of Intermediate 1 (0.75 g, 4.3 mmol) and 4% (1,2,4 -triazol-4-yl)phenylhydrazine (0.75 g, 4.3 mmol), in 4% H₂SO₄ (50 ml) was heated at reflux for 22 h. The mixture was cooled to room temperature, basified with K₂CO₃ and extracted with EtOAc (3×100 ml). The resultant crude product was chromatographed on silica gel eluting with CH₂Cl₂/MeOH/NH₃ (40:8:1) to give the title-product (0.12 g). The oxalate hydrate salt was prepared; mp 218°–220° C. (Found: C, 52.86; H, 5.63; N, 17.98. C₁₇H₁₅N₅.C₂H₂O₄ 1.6H₂O requires C, 52.87; H, 5.79; N, 18.13%.) δ (360 MHz, D₂O) 2.36–2.63 (2H, m, CH₂), 3.06 (2H, t, J=7.0 Hz, CH₂), 3.52 (2H, t, J=7.0 Hz, CH₂), 4.01–4.22 (4H, m, 2 of CH₂), 7.21 (1H, dd, J=2.0 and 8.6 Hz, Ar—H), 7.39 (1H, s, Ar—H), 7.56 (1H, d, J=8.6 Hz, Ar—H), 7.62 (1H, d, J=2.0 Hz, Ar—H), 8.91 (2H, s, Ar—H).

EXAMPLE 8

N-2-[5-(1,2,4-Triazol-4-yl)-1H-indol-3-yl]ethylpyrrolidine. Oxalate

INTERMEDIATE 8

4-(1-Pyrrolidinyl)butanal dimethylacetal

A solution of 4-chlorobutanal diethylacetal (10 g, 55.40 mmol) in pyrrolidine (40 ml) was heated at reflux for 16 h. The solvent was removed under vacuum, 2N NaOH (50 ml) added and the mixture extracted with CH₂Cl₂ (100ml). The extract was dried and evaporated and the residue distilled (74° C., 1 mmHg) to give the title-product (8.8 g, 74%). δ (250 MHz, D₆—DMSO) 1.10 (6H, t, J=7.5 Hz, 2 of CH₃), 1.34–1.70 (8H, m, 4 of CH₂), 2.28–2.40 (6H, m, 3 of CH₂), 3.26–3.60 (4H, m, 2 of CH₂O), 4.46 (1H, t, J=5.5Hz, CHO).

N-2-[5-(1,2,4-Triazol-4-yl)-1H-indol-3-yl]ethylpyrrolidine. Oxalate

The title-compound was prepared from Intermediates 6 and 8 using the procedure described for Example 7. The oxalate salt was prepared; mp 244°–245° C.; (Found: C, 62.25; H, 6.06; N, 21.33. $C_{16}H_{19}N_5 \cdot 0.5(C_2H_2O_4) \cdot 0.1H_2O$ requires C, 62.22; H, 6.20; N, 21.34%); δ (250 MHz, $D_2O$) 1.78–1.86 (4H, m, 2 of $CH_2$), 2.86–3.08 (8H, m, 4 of $CH_2$), 7.32 (1H, dd, J=2.0 and 8.6 Hz, Ar—H), 7.36 (1H, d, J=2.0 Hz, Ar—H), 7.50 (1H, d, J=8.6 Hz, Ar—H), 7.85 (1H, d, J=2.0 Hz, Ar—H), 9.02 (2H, s, Ar—H), 11.18 (1H, s, indole NH).

EXAMPLE 9

Tablet Preparation

Tablets containing 1.0, 2.0, 25.0, 26.0, 50.0 and 100.0 mg, respectively of the following compounds are prepared as illustrated below:

N-2-[5-(1,2,4-Triazol-1-ylmethyl)-1H-indol-3-yl]ethyl azetidine. Hydrogen Oxalate.

N-2-[5-(1,2,4-Triazol-1-yl)-1H-indol-3-yl]ethylazetidine. Bisoxalate.

N-Methyl-3-[5-(1,2,4-triazol-1-ylmethyl)-1H-indol-3-yl] methylazetidine. 0.65 Oxalate.

(±)N-Methyl-2-[5-(1,2,4-triazol-1-ylmethyl)-1H-indol-3-yl]methylpyrrolidine. Hydrogen Oxalate. 0.2 Hydrate.

(2R)N-Methyl-2-[5-(1,2,4-triazol-4-yl)-1H-indol-3-yl] methylpyrrolidine. 1.3 Benzoate. 0.9 Hydrate.

3-[trans-1-(Dimethylamino)cyclobutan-3-yl]-5-[(1,2,4-triazol-1-yl) methyl]-1H-indole and 3-[cis-1-(Dimethylamino)cyclobutan-3-yl]-5-[(1,2,4-triazol-1-yl) methyl]-1H-indole. Hydrogen Oxalates.

N-2-[5-(1,2,4-Triazol-4-yl)-1H-indol-3-yl]ethylazetidine. Oxalate. 1.6 Hydrate

N-2-[5-(1,2,4-Triazol-4-yl)-1H-indol-3-yl]ethylpyrrolidine. Oxalate.

| TABLE FOR DOSES CONTAINING FROM 1–25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

We claim:
1. A compound of formula I, or a pharmaceutically acceptable salt or prodrug thereof:

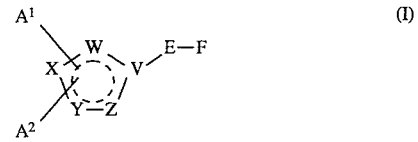

wherein the broken circle represents two non-adjacent double bonds in any position in the five-membered ring;

two, three or four of V, W, X, Y and Z represent nitrogen and the remainder represent carbon provided that, when two of V, W, X, Y and Z represent nitrogen and the remainder represent carbon, then the said nitrogen atoms are in non-adjacent positions within the five-membered ring;

$A^1$ represents hydrogen, hydrocarbon selected from the group consisting of: $C_{1-6}$ alkyl, $C_{2-6}$ alkenyl, $C_{2-6}$ alkynyl, $C_{3-7}$ cycloalkyl, $C_{3-7}$ cycloalkyl ($C_{1-6}$) alkyl, aryl and aryl. ($C_{1-6}$) alkyl, where aryl is phenyl; a heterocyclic group selected from the group consisting of: $C_{3-7}$ heterocycloalkyl, $C_{3-7}$ heterocycloalkyl ($C_{1-6}$) alkyl, heteroaryl and heteroaryl ($C_{1-6}$) alkyl wherein heterocycloalkyl is selected from: azetidinyl, pyrrolidyl, piperidyl, piperazinyl and morpholinyl; and heteroaryl is selected from: pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl; halogen, cyano, trifluoromethyl, —$OR^x$, —$SR^x$, —$NR^xR^y$, —$NR^xCOR^y$, —$NR^xCO_2R^y$, —$NR^xSO_2R^y$, or —$NR^zCTNR^xR^y$;

$A^2$ represents a non-bonded electron pair when four of V, W, X, Y and Z represent nitrogen and the other represents carbon; or, when two or three of V, W, X, Y and Z represent nitrogen and the remainder represent carbon, $A^2$ represents hydrogen, hydrocarbon, a heterocyclic group, halogen, cyano, trifluoromethyl, —$OR^x$, —$SR^x$, —$NR^xR^y$, —$NR^xCOR^y$, —$NR^xCO_2R^y$, —$NR^xSO_2R^y$, or —$NR^zCTNR^xR^y$; wherein $A^1$ and $A^2$, where $A^2$ is not a non-bonded electron pair can be optionally substituted with trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$) alkylamino-carbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$) alkylaminosulphonylmethyl;

E represents a bond or a straight or branched alkylene chain containing from 1 to 4 carbon atoms;

F represents a group of formula

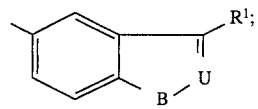

U represents nitrogen or C—$R^2$;

B represents oxygen, sulphur or N—$R^3$;

$R^1$ represents a group of formula (i), (ii) or (iii):

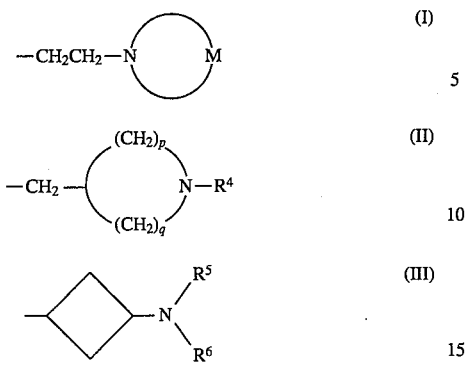

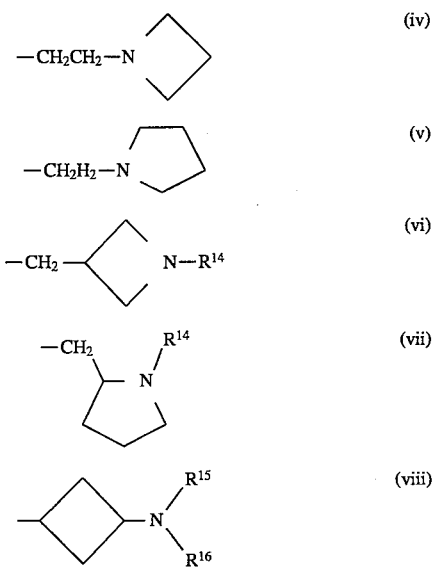

in which

M represents the residue of an azetidine, pyrrolidine or piperidine ring wherein formula (i) represents azetidin-1-ylethyl, pyrrolidin-1-ylethyl or piperidin-1-ylethyl;

p is zero or 1 and q is an integer from 1 to 4, provided that the sum of p+q is 2, 3 or 4;

$R^2$, $R^3$, $R^4$, $R^5$ and $R^6$ independently represent hydrogen or $C_{1-6}$ alkyl;

$R^x$ and $R^y$ independently represent hydrogen, hydrocarbon or a heterocyclic group, both as defined above, or $R^x$ and $R^y$ together represent a $C_{2-6}$ alkylene group;

$R^z$ represents hydrogen, hydrocarbon or a heterocyclic group, both as defined above;

T represents oxygen, sulphur or a group of formula =N—G; and

G represents hydrocarbon, a heterocyclic group, both as defined above, or an electron-withdrawing group.

2. A compound of formula I as claimed in claim 1, or a pharmaceutically acceptable salt or prodrug thereof, wherein $R^1$ represents a group of formula (i) or (ii) as defined in claim 1.

3. A compound as claimed in claim 1 represented by formula II, or a pharmaceutically acceptable salt or prodrug thereof:

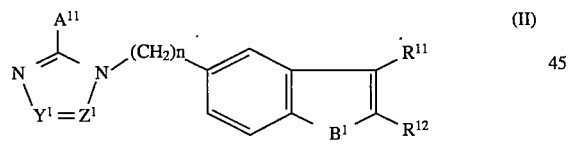

wherein $Y^1$ represents nitrogen or $A^{12}$—C;

$Z^1$ represents nitrogen or CH;

n is zero, 1, 2 or 3;

$B^1$ represents oxygen, sulphur or N—$R^{13}$;

$A^{11}$ and $A^{12}$ independently represent $C_{1-6}$ alkyl, $C_{2-6}$ alkenyl, $C_{2-6}$ alkynyl, $C_{3-7}$ cycloalkyl, aryl, aryl ($C_{1-6}$) alkyl, $C_{3-7}$ heterocycloalkyl, heteroaryl, heteroaryl ($C_{1-6}$) alkyl, $C_{1-6}$ alkoxy, $C_{1-6}$ alkylthio, $C_{1-6}$ alkylamino or di ($C_{1-6}$) alkylamino, any of which groups may be optionally substituted as defined in claim 1 for $A^1$ and $A^2$; or hydrogen, halogen, cyano, trifluoromethyl or amino;

$R^{11}$ represents a group of formula (iv), (v), (vi), (vii) or (viii):

and $R^{12}$, $R^{13}$, $R^{14}$, $R^{15}$ and $R^{16}$ independently represent hydrogen or $C_{1-6}$ alkyl.

4. A compound as claimed in claim 3 wherein $A^{11}$ and $A^{12}$ both represent hydrogen.

5. A compound as claimed in claim 3 wherein $R^{12}$ and $R^{13}$ both represent hydrogen.

6. A compound as claimed in claim 3 wherein $R^{14}$, $R^{15}$ and $R^{16}$ each represents methyl.

7. A compound as claimed in claim 1 selected from:

N-2-[5-(1,2,4-triazol-1-ylmethyl)-1H-indol-3-yl]ethylazetidine;

N-2-[5-(1,2,4-triazol-1-yl)-1H-indol-3-yl]ethylazetidine;

N-methyl-3-[5-(1,2,4-triazol-1-ylmethyl)-1H-indol-3-yl]methylazetidine;

N-methyl-2-[5-(1,2,4-triazol-1-ylmethyl)-1H-indol-3-yl]methylpyrrolidine;

(2R)-N-methyl-2-[5-(1,2,4-triazol-4-yl)-1H-indol-3-yl]methylpyrrolidine;

3-[cis-1-(N,N-dimethylamino)cyclobutan-3-yl]-5-(1,2,4-triazol-1-ylmethyl)-1H-indole;

3-[trans-1-(N,N-dimethylamino)cyclobutan-3-yl]-5-(1,2,4-triazol-1-ylmethyl)-1H-indole;

N-2-[5-(1,2,4-triazol-4-yl)-1H-indol-3-yl]ethylazetidine;

N-2-[5-(1,2,4-triazol-4-yl)-1H-indol-3-yl]ethylpyrrolidine;

or a pharmaceutically acceptable salt or prodrug thereof.

8. A pharmaceutical composition comprising a compound of formula I as defined in claim 1 or a pharmaceutically acceptable salt thereof or a prodrug thereof in association with a pharmaceutically acceptable carrier.

9. A method for the treatment of migraine and associated conditions selected from the group consisting of: cluster headache, chronic paroxysmal hemicrania, headache associated with vascular disorders, tension headache and pediatric migraine for which a selective agonist of 5-$HT_1$-like receptors is indicated, which method comprises administering to a patient in need of such treatment an effective amount of a compound of formula I as defined in claim 1, or a pharmaceutically acceptable salt thereof or a prodrug thereof.

* * * * *